United States Patent
Kao et al.

(10) Patent No.: US 10,435,447 B2
(45) Date of Patent: Oct. 8, 2019

(54) BACTERIOCIDAL PEPTIDES AND USES THEREOF

(71) Applicant: INDIANA UNIVERSITY RESEARCH AND TECHNOLOGY CORPORATION, Indianapolis, IN (US)

(72) Inventors: C. Cheng Kao, Bloomington, IN (US); Xiaoyan Lin, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/778,673

(22) PCT Filed: Nov. 23, 2016

(86) PCT No.: PCT/US2016/063612
§ 371 (c)(1),
(2) Date: May 24, 2018

(87) PCT Pub. No.: WO2017/091734
PCT Pub. Date: Jun. 1, 2017

(65) Prior Publication Data
US 2018/0355005 A1    Dec. 13, 2018

Related U.S. Application Data

(60) Provisional application No. 62/260,242, filed on Nov. 25, 2015.

(51) Int. Cl.
*C07K 14/47* (2006.01)
*A01G 25/02* (2006.01)
*A61K 38/04* (2006.01)
*A61K 38/17* (2006.01)
*A61K 38/00* (2006.01)

(52) U.S. Cl.
CPC .......... *C07K 14/4742* (2013.01); *A01G 25/02* (2013.01); *A61K 38/04* (2013.01); *C07K 14/4723* (2013.01); *A61K 38/00* (2013.01); *A61K 38/1751* (2013.01); *C07K 2319/00* (2013.01)

(58) Field of Classification Search
None
See application file for complete search history.

(56) References Cited

U.S. PATENT DOCUMENTS

| 7,846,895 B2 * | 12/2010 | Eckert ...................... C07K 7/06 514/2.6 |
| 2007/0231833 A1 | 10/2007 | Arcidiacono et al. |
| 2008/0119405 A1 | 5/2008 | Zhang et al. |
| 2009/0155335 A1 | 6/2009 | O'Shaughnessey et al. |

FOREIGN PATENT DOCUMENTS

WO    2015183683 A2    12/2015

OTHER PUBLICATIONS

Wang (Journal of Biological Chemistry vol. 283, No. 47, 2008,pp. 32637-32643).*
UniProtKB/Swiss-Prot: P49928.1, accessed Jan. 19, 2019.*
PCT International Search Report and Written Opinion completed by the ISA/US on Apr. 5, 2017 and issued in connection with PCT/US2016/063612.
International Preliminary Examination Report mailed from the IPEA/US dated Feb. 15, 2018 and issued in connection with PCT/US2016/063612.
Dawson, et al. Analogues of Peptide SMAP-29 with Comparable Antimicrobial Potency and Reduced Cytotoxicity. International Journal of Antimicrobial Agents. 2011, vol. 37, pp. 432-437, see Table 1.
Travis, et al. Batericidal Activity of Mammalian Cathelicidin-Derived Peptides. Infect Immun. 200, 68(5): 2748-2755; Abstract.
Singh, D., et al. "The Human Antimicrobial Peptide LL-37, but Not the Mouse Ortholog, mCRAMP, Can Stimulate Signaling by Poly (I:C) through a FPRL1-dependent Pathway" J. Biol. Chem. 2013, 288: 8258-8268.
Pikal, M. "Freeze-Drying of Proteins Part II: Formulation Selection" M. Biopharm. 3(9)26-30 (1990).
Arakawa, T., et al. "Protein-Solvent Interactions in Pharmaceutical Formulations" Pharm. Res., 8(3):285-291 (1991).
Zanetti, M. "Cathelicidins, multifunctional peptides of the innate immunity" J. Leuk. Biol. 2004, 75: 39-48.
Remington's Pharmaceutical Sciences, 19th edition, Mack Publishing Co., 1995; Reference Textbook; available upon request.

* cited by examiner

*Primary Examiner* — James H Alstrum-Acevedo
*Assistant Examiner* — Tara L Martinez

(57) ABSTRACT

Peptide compositions having bacteriocidal peptides are described. Also described is a method of bacterial infections using compositions comprising bacteriocidal peptides or modified peptides with structural relationships to cathelicidins.

4 Claims, 11 Drawing Sheets

Specification includes a Sequence Listing.

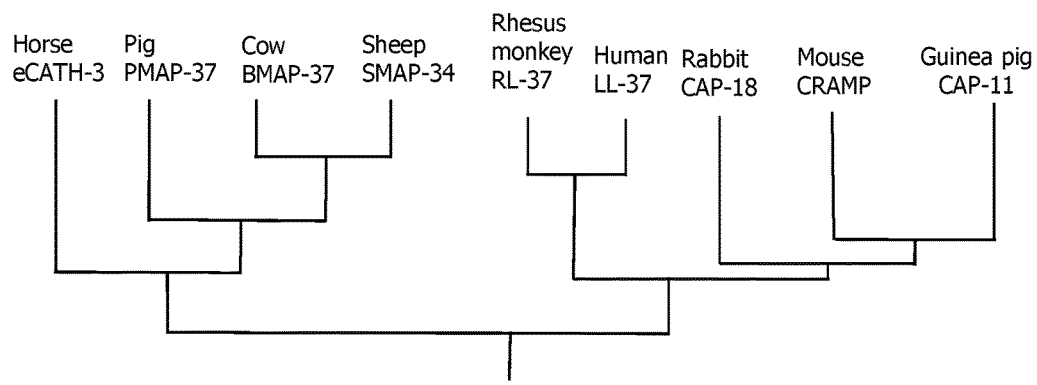

Fig. 1A

| Peptide | #AAs | Sequence | |
|---|---|---|---|
| LL-37 | 37 | LLGDFFRKSKEKIGKEFKRIVQRIKDFLRNLVPRTES | (SEQ ID NO: 1) |
| RL-37 | 37 | RLGNFFRKVKEKIGGGLKKVGQKIKDFLGNLVPRTAS | (SEQ ID NO: 2) |
| CAP-18 | 37 | GLRKRLRKFRNKIKEKLKKIGQKIQGLLPKLAPRTDY | (SEQ ID NO: 3) |
| CRAMP | 34 | GLLRKGGEKIGEKLKKIGQKIKNFFQKLVPQPEQ | (SEQ ID NO: 4) |
| CAP-11 | 43 | GLRKKFRKTRKRIQKLGRKIGKTGRKVWKAWREYGQIPYPCRI | (SEQ ID NO: 5) |
| SMAP-34 | 34 | GLFGRLRDSLQRGGQKILEKAERIWCKIKDIFR | (SEQ ID NO: 6) |
| BMAP-34 | 34 | GLFRRLRDSIRRGQQKILEKARRIGERIKDIFRG | (SEQ ID NO: 7) |
| PMAP-37 | 37 | GLLSRLRDFLSDRGRRLGEKIERIGQKIKDLSEFFQS | (SEQ ID NO: 8) |
| eCATH-3 | 40 | KRFHSVGSLIQRHQQMIRDKSEATRHGIRIITRPKLLLAS | (SEQ ID NO: 9) |

Fig. 1B

| Peptide | # strains inhibited | | | | | |
|---|---|---|---|---|---|---|
| | K. p. | S. m. | E. cl. | E. co | P. a. | Total |
| LL-37 | 0/4 | 0/3 | 0/2 | 0/6 | 0/4 | 0/19 |
| eCATH-3 | 0/4 | 0/3 | 0/2 | 0/6 | 0/4 | 0/19 |
| SMAP-34 | 0/4 | 0/3 | 0/2 | 0/6 | 0/4 | 0/19 |
| eCATH-2 | 0/4 | 0/3 | 0/2 | 0/6 | 0/4 | 0/19 |
| CRAMP | 0/4 | 0/3 | 1/2 | 1/6 | 0/4 | 2/19 |
| eCATH-2 | 0/4 | 0/3 | 1/2 | 1/6 | 0/4 | 2/19 |
| PMAP-23 | 0/4 | 0/3 | 1/2 | 1/6 | 0/4 | 2/19 |
| PMAP-37 | 0/4 | 0/3 | 1/2 | 2/6 | 1/4 | 4/19 |
| RL-37 | 3/4 | 0/3 | 1/2 | 2/6 | 1/4 | 7/19 |
| BMAP-28 | 0/4 | 0/3 | 2/2 | 4/6 | 1/4 | 7/19 |
| CAP-18 | 4/4 | 0/3 | 1/2 | 3/6 | 3/4 | 11/19 |
| eCATH-1 | 4/4 | 0/3 | 1/2 | 3/6 | 3/4 | 11/19 |
| BMAP-34 | 4/4 | 0/3 | 2/2 | 4/6 | 3/4 | 13/19 |
| PMAP-36 | 4/4 | 1/3 | 2/2 | 5/6 | 4/4 | 16/19 |
| CAP-11 | 4/4 | 1/3 | 2/2 | 5/6 | 4/4 | 16/19 |
| SMAP-29 | 4/4 | 1/3 | 2/2 | 5/6 | 4/4 | 16/19 |
| BMAP-27 | 4/4 | 2/3 | 2/2 | 5/6 | 4/4 | 17/19 |

Fig. 3A

| Peptide | # strains inhibited | | | | | |
|---|---|---|---|---|---|---|
| | *K. p.* | *S. m.* | *E. cl.* | *E. co* | *P. a.* | Total |
| LL-37 | 0/4 | 0/3 | 0/2 | 0/6 | 0/4 | 0/19 |
| LL-29 | 0/4 | 0/3 | 1/2 | 2/6 | 0/4 | 3/19 |
| CAP-11 | 4/4 | 1/3 | 2/2 | 5/6 | 4/4 | 16/19 |
| CAP-11V1 | 4/4 | 1/3 | 2/2 | 5/6 | 4/4 | 16/19 |

| Peptide | # strains inhibited | | | | | |
|---|---|---|---|---|---|---|
| | *K. p.* | *S. m.* | *E. cl.* | *E. co* | *P. a.* | Total |
| LL-29 | 0/4 | 0/3 | 1/2 | 2/6 | 0/4 | 3/19 |
| LL-29V2 | 0/4 | 0/3 | 1/2 | 3/6 | 0/4 | 4/19 |
| LL-29V | 4/4 | 1/3 | 1/2 | 4/6 | 1/4 | 11/19 |
| SMAP-29 | 4/4 | 1/3 | 2/2 | 5/6 | 4/4 | 16/19 |
| SMAP-29V | 4/4 | 1/3 | 1/2 | 5/6 | 2/4 | 13/19 |

|          | RBC lysis | % strains inhibited |
|----------|-----------|---------------------|
| CAP11-V3 | 0.4       | 31.6                |
| eCATH-3  | 0.8       | 0                   |
| eCATH-1  | 1.8       | 57.9                |
| PAMP-23  | 1.9       | 10.5                |
| SMAP-29V | 2.3       | 84.2                |
| CAP-18   | 2.5       | 31.6                |
| SMAP-29  | 5.6       | 84.2                |
| eCATH-2  | 7.3       | 10.5                |
| LL-29V2  | 8.9       | 21                  |
| CAP-11V1 | 9.2       | 84.2                |
| LL-29    | 9.7       | 15.8                |
| SMAP-27  | 10        | 89.5                |
| CAP-11V2 | 12.2      | 84.2                |
| LL-29V   | 19.4      | 57.9                |
| PAMP-36  | 27.8      | 84.2                |
| LL-37    | 34.7      | 0                   |
| CAP-11   | 38        | 84.2                |
| BMAP-28  | 66.2      | 36.8                |
| SMAP-34  | 60.9      | 0                   |
| PMAP-37  | 69.4      | 21.1                |

Fig. 5A

|         | RBC lysis | # strains killed |
|---------|-----------|------------------|
| SMAP-29 | 5.6       | 16/19            |
| SMAP-29B| 2.3       | 16/19            |
| SMAP-29D| 1.5       | 16/19            |
Fig. 6A
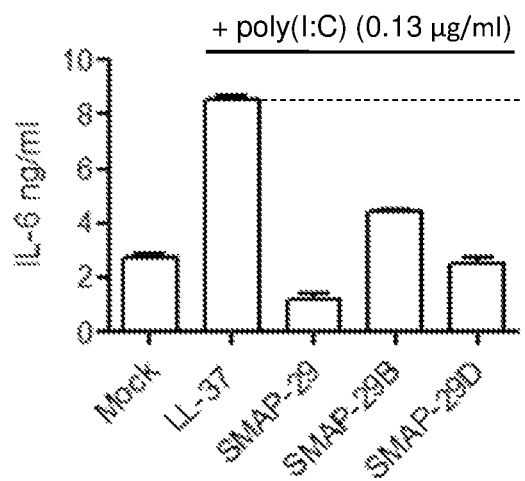
Fig. 6B
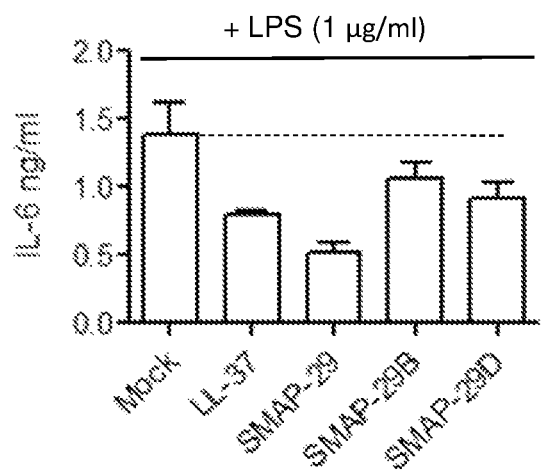
Fig. 6C Table 1. Minimal inhibitory concentrations of select antimicrobial peptides against 19 Gram-negative strains

Fig. 8

SEQUENCE LISTING

```
<160> NUMBER OF SEQ ID NOS: 26

<210> SEQ ID NO 1
<211> LENGTH: 37
<212> TYPE: PRT
<213> ORGANISM: Homo sapiens

<400> SEQUENCE: 1

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 2
<211> LENGTH: 37
<212> TYPE: PRT
<213> ORGANISM: Macaca mulatta

<400> SEQUENCE: 2

Arg Leu Gly Asn Phe Phe Arg Lys Val Lys Glu Lys Ile Gly Gly Gly
1               5                   10                  15

Leu Lys Lys Val Gly Gln Lys Ile Lys Asp Phe Leu Gly Asn Leu Val
            20                  25                  30

Pro Arg Thr Ala Ser
        35

<210> SEQ ID NO 3
<211> LENGTH: 37
<212> TYPE: PRT
<213> ORGANISM: Oryctolagus cuniculus

<400> SEQUENCE: 3

Gly Leu Arg Lys Arg Leu Arg Lys Phe Arg Asn Lys Ile Lys Glu Lys
1               5                   10                  15

Leu Lys Lys Ile Gly Gln Lys Ile Gln Gly Leu Leu Pro Lys Leu Ala
            20                  25                  30

Pro Arg Thr Asp Tyr
        35

<210> SEQ ID NO 4
<211> LENGTH: 34
```

```
<212> TYPE: PRT
<213> ORGANISM: Mus musculus

<400> SEQUENCE: 4

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 5
<211> LENGTH: 43
<212> TYPE: PRT
<213> ORGANISM: Cavia porcellus

<400> SEQUENCE: 5

Gly Leu Arg Lys Lys Phe Arg Lys Thr Arg Lys Arg Ile Gln Lys Leu
1               5                   10                  15

Gly Arg Lys Ile Gly Lys Thr Gly Arg Lys Val Trp Lys Ala Trp Arg
            20                  25                  30

Glu Tyr Gly Gln Ile Pro Tyr Pro Cys Arg Ile
        35                  40

<210> SEQ ID NO 6
<211> LENGTH: 33
<212> TYPE: PRT
<213> ORGANISM: Ovis aries

<400> SEQUENCE: 6

Gly Leu Phe Gly Arg Leu Arg Asp Ser Leu Gln Arg Gly Gly Gln Lys
1               5                   10                  15

Ile Leu Glu Lys Ala Glu Arg Ile Trp Cys Lys Ile Lys Asp Ile Phe
            20                  25                  30

Arg

<210> SEQ ID NO 7
<211> LENGTH: 34
<212> TYPE: PRT
<213> ORGANISM: Bos taurus

<400> SEQUENCE: 7

Gly Leu Phe Arg Arg Leu Arg Asp Ser Ile Arg Arg Gly Gln Gln Lys
1               5                   10                  15

Ile Leu Glu Lys Ala Arg Arg Ile Gly Glu Arg Ile Lys Asp Ile Phe
            20                  25                  30

Arg Gly

<210> SEQ ID NO 8
<211> LENGTH: 37
<212> TYPE: PRT
<213> ORGANISM: Sus scrofa

<400> SEQUENCE: 8

Gly Leu Leu Ser Arg Leu Arg Asp Phe Leu Ser Asp Arg Gly Arg Arg
1               5                   10                  15

Leu Gly Glu Lys Ile Glu Arg Ile Gly Gln Lys Ile Lys Asp Leu Ser
            20                  25                  30

Glu Phe Phe Gln Ser
        35
```

<210> SEQ ID NO 9
<211> LENGTH: 40
<212> TYPE: PRT
<213> ORGANISM: Equus caballus

<400> SEQUENCE: 9

```
Lys Arg Phe His Ser Val Gly Ser Leu Ile Gln Arg His Gln Gln Met
1               5                   10                  15

Ile Arg Asp Lys Ser Glu Ala Thr Arg His Gly Ile Arg Ile Ile Thr
            20                  25                  30

Arg Pro Lys Leu Leu Leu Ala Ser
        35                  40
```

<210> SEQ ID NO 10
<211> LENGTH: 27
<212> TYPE: PRT
<213> ORGANISM: Equus caballus

<400> SEQUENCE: 10

```
Lys Arg Arg His Trp Phe Pro Leu Ser Phe Gln Glu Phe Leu Glu Gln
1               5                   10                  15

Leu Arg Arg Phe Arg Asp Gln Leu Pro Phe Pro
            20                  25
```

<210> SEQ ID NO 11
<211> LENGTH: 23
<212> TYPE: PRT
<213> ORGANISM: Sus scrofa

<400> SEQUENCE: 11

```
Arg Ile Ile Asp Leu Leu Trp Arg Val Arg Pro Gln Lys Pro Lys
1               5                   10                  15

Phe Val Thr Val Trp Val Arg
            20
```

<210> SEQ ID NO 12
<211> LENGTH: 28
<212> TYPE: PRT
<213> ORGANISM: Bos taurus

<400> SEQUENCE: 12

```
Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile Gly
            20                  25
```

<210> SEQ ID NO 13
<211> LENGTH: 26
<212> TYPE: PRT
<213> ORGANISM: Equus caballus

<400> SEQUENCE: 13

```
Lys Arg Phe Gly Arg Leu Ala Lys Ser Phe Leu Arg Met Arg Ile Leu
1               5                   10                  15

Leu Pro Arg Arg Lys Ile Leu Leu Ala Ser
            20                  25
```

<210> SEQ ID NO 14
<211> LENGTH: 37
<212> TYPE: PRT
<213> ORGANISM: Sus scrofa

<400> SEQUENCE: 14

Val Gly Arg Phe Arg Arg Leu Arg Lys Thr Arg Lys Arg Leu Lys
1               5                   10                  15

Lys Ile Gly Lys Val Leu Lys Trp Ile Pro Pro Ile Val Gly Ser Ile
                20                  25                  30

Pro Leu Gly Cys Gly
            35

<210> SEQ ID NO 15
<211> LENGTH: 29
<212> TYPE: PRT
<213> ORGANISM: Ovis aries

<400> SEQUENCE: 15

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
                20                  25

<210> SEQ ID NO 16
<211> LENGTH: 27
<212> TYPE: PRT
<213> ORGANISM: Bos taurus

<400> SEQUENCE: 16

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
                20                  25

<210> SEQ ID NO 17
<211> LENGTH: 29
<212> TYPE: PRT
<213> ORGANISM: Homo sapiens

<400> SEQUENCE: 17

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg
                20                  25

<210> SEQ ID NO 18
<211> LENGTH: 34
<212> TYPE: PRT
<213> ORGANISM: Cavia porcellus

<400> SEQUENCE: 18

Gly Leu Arg Lys Lys Phe Arg Lys Thr Arg Lys Arg Ile Gln Lys Leu
1               5                   10                  15

Gly Arg Lys Ile Gly Lys Thr Gly Arg Lys Val Trp Lys Ala Trp Arg
                20                  25                  30

Glu Tyr

<210> SEQ ID NO 19
<211> LENGTH: 29
<212> TYPE: PRT
<213> ORGANISM: Homo sapiens

<400> SEQUENCE: 19

Leu Leu Gly Ala Phe Phe Arg Lys Ser Lys Glu Lys Ile Gly Lys Ala
1               5                   10                  15

```
Phe Lys Arg Ile Val Gln Arg Ile Lys Asp Phe Leu Arg
            20                  25
```

<210> SEQ ID NO 20
<211> LENGTH: 29
<212> TYPE: PRT
<213> ORGANISM: Homo sapiens

<400> SEQUENCE: 20

```
Leu Leu Gly Ala Phe Phe Arg Lys Ser Lys Ala Lys Ile Gly Lys Ala
1               5                   10                  15

Phe Lys Arg Ile Val Gln Arg Ile Lys Ala Phe Leu Arg
            20                  25
```

<210> SEQ ID NO 21
<211> LENGTH: 29
<212> TYPE: PRT
<213> ORGANISM: Ovis aries

<400> SEQUENCE: 21

```
Arg Gly Leu Arg Arg Leu Gly Arg Lys Ile Ala His Glu Val Lys Lys
1               5                   10                  15

Tyr Gly Pro Thr Val Leu Arg Asp Ile Arg Ile Ala Gly
            20                  25
```

<210> SEQ ID NO 22
<211> LENGTH: 43
<212> TYPE: PRT
<213> ORGANISM: Cavia porcellus

<400> SEQUENCE: 22

```
Gly Leu Arg Lys Lys Phe Arg Glu Thr Arg Lys Glu Ile Gln Lys Leu
1               5                   10                  15

Gly Glu Lys Ile Gly Lys Thr Gly Arg Lys Val Trp Lys Asp Trp Arg
            20                  25                  30

Glu Tyr Gly Gln Ile Pro Tyr Pro Cys Arg Ile
            35                  40
```

<210> SEQ ID NO 23
<211> LENGTH: 43
<212> TYPE: PRT
<213> ORGANISM: Cavia porcellus

<400> SEQUENCE: 23

```
Gly Leu Arg Lys Lys Phe Arg Glu Thr Arg Lys Glu Ile Gln Lys Leu
1               5                   10                  15

Gly Arg Lys Ile Gly Lys Thr Gly Arg Lys Val Trp Lys Ala Trp Arg
            20                  25                  30

Glu Tyr Gly Gln Ile Pro Tyr Pro Cys Arg Ile
            35                  40
```

<210> SEQ ID NO 24
<211> LENGTH: 29
<212> TYPE: PRT
<213> ORGANISM: Ovis aries

<400> SEQUENCE: 24

```
Arg Gly Leu Arg Arg Leu Gly Arg Lys Ile Ala His Gly Val Lys Lys
1               5                   10                  15

Cys Gly Pro Thr Val Leu Arg Ile Ile Arg Ile Ala Gly
            20                  25
```

```
<210> SEQ ID NO 25
<211> LENGTH: 30
<212> TYPE: PRT
<213> ORGANISM: Ovis aries

<400> SEQUENCE: 25

Arg Gly Leu Arg Arg Leu Gly Arg Lys Ile Ala His Gly Val Lys Lys
1               5                   10                  15

Cys Gly Pro Thr Val Leu Arg Ile Ile Arg Ile Ala Gly Cys
            20                  25                  30

<210> SEQ ID NO 26
<211> LENGTH: 29
<212> TYPE: PRT
<213> ORGANISM: Ovis aries

<400> SEQUENCE: 26

Arg Gly Leu Arg Arg Leu Gly Arg Lys Ile Ala His Gly Val Lys Lys
1               5                   10                  15

Leu Gly Pro Thr Val Leu Arg Ile Ile Arg Ile Ala Gly
            20                  25
```

BACTERIOCIDAL PEPTIDES AND USES THEREOF

CROSS-REFERENCE TO RELATED APPLICATIONS

This application is a national stage entry under 35 USC § 371 of PCT International Application No. PCT/US2016/063612, filed Nov. 23, 2016, and claims priority under 35 USC § 119(e) to U.S. Provisional Patent Application No. 62/260,242 filed Nov. 25, 2015, the disclosures of which are expressly incorporated by reference in their entirety.

SEQUENCE LISTING

The instant application contains a Sequence Listing which has been submitted electronically in ASCII format and is hereby incorporated by reference in its entirety. Said ASCII copy, created on Nov. 15, 2016, is named 29920_260129_SL.txt and is 9,390 bytes.

FIELD OF THE INVENTION

This disclosure is related to the antimicrobial peptides, sometimes called bacteriocidal peptides, and their derivatives from the cathelicidin family. Specifically, peptides and preferred motifs that diminish detrimental pro-inflammatory responses and increased direct killing of microbes were identified. The making and using of such peptides with antibiotics to treat Gram-negative bacteria infection with reduced peptides/antibiotics dosage are within the scope of this disclosure.

BACKGROUND

Cathelicidin-related antimicrobial peptides are a family of polypeptides produced by macrophages and polymorphonuclear leukocytes (PMNs), and epithelial cells such as keratinocytes. Cathelicidins serve a critical role in mammalian innate immune defense against invasive bacterial infection. The peptides of the cathelicidin family are classified as antimicrobial peptides (AMPs).

Cathelicidin peptides have been isolated from many different species of mammals, including but not limited to humans, monkeys, mice, rats, rabbits, guinea pigs, pandas, pigs, cattle, frogs, sheep, goats, chickens, and horses. Some species produce more than one cathelicidin. All cathelicidins are enriched for positively-charged amino acids, but the sequences for the cathelicidins produced by different animals have highly varied sequences.

Currently identified cathelicidins include but not limited to the following:
Human: hCAP-18/LL-37 (SEQ ID NO: 1)
Rhesus Monkey: RL-37 (SEQ ID NO: 2)
Mice: CRAMP (SEQ ID NO: 4), (Cathelicidin-related Antimicrobial Peptide)
Rats: rCRAMP
Rabbits: CAP-18 (SEQ ID NO: 3)
Guinea Pig: CAP-11 (SEQ ID NO: 5)
Pigs: PR-39, Prophenin, PMAP-23,36,37
Cattle: BMAP-27,28,34 (Bovine Myeloid Antimicrobial Peptides); Bac5, Bac7
Horses: eCATH-1 (SEQ ID NO: 13), eCATH-2 (SEQ ID NO: 10), eCATH-3 (SEQ ID NO: 9)
Frogs: cathelicidin-AL (found in *Amolops loloensis*)
Sheep: SMAP-29 (SEQ ID NO: 15)
Chickens: Four cathelicidins, fowlicidins 1,2,3 and cathelicidin Beta-1

Cathelicidins range in size from 12 to 80 amino acid residues and have a wide range of structures. Most cathelicidins are linear peptides with 23-37 amino acid residues, and fold into amphipathic α-helices. In addition, some cathelicidins contain beta-strand structures or can be stabilized by one or two disulfide bonds. Larger cathelicidin peptides (39-80 amino acid residues) are also possible. These larger cathelicidin peptides display repetitive proline motifs forming extended polyproline-type structures.

SUMMARY

This disclosure provides a pharmaceutical composition of a modified peptide derived from a native cathelicidin, such modified peptide has clustered positively charged basic residues within its N-terminal sequence, and limited acidic residues throughout the peptide sequence. In some embodiments, the native cathelicidin is selected from the mammal group consisting of horse, pig, cow, sheep, goat, rhesus monkey, human, rabbit, mouse, rate and guinea pig. For example, these native cathelicidin peptides can selected from the group group consisting of eCATH-1 (SEQ ID NO: 13), eCATH-2 (SEQ ID NO: 10), eCATH-3 (SEQ ID NO: 9), PMAP-23 (SEQ ID NO: 11), PMAP-36 (SEQ ID NO: 14), PMAP-37 (SEQ ID NO: 8), BMAP-27 (SEQ ID NO: 16), BMAP-28 (SEQ ID NO: 12), BMAP-34 (SEQ ID NO: 7), SMAP-29 (SEQ ID NO: 15), SMAP-34 (SEQ ID NO: 6), chMAP-28, chMAP-34, RL-37 (SEQ ID NO: 2), LL-37 (SEQ ID NO: 1), hCAP-18, CRAMP (SEQ ID NO: 4), rCRAMP, CAP-11 (SEQ ID NO: 5) and CAP-18 (SEQ ID NO: 3).

In a preferred embodiment, the aforementioned composition of a modified peptide, sometimes called a bacteriocidal peptide, has at least 30% clustered basic residues within the N-terminal sequence, and no more than 10% acidic amino acids of the total residues.

In some embodiments, the aforementioned pharmaceutical composition comprising the modified peptide:
 a. lacks a pro-inflammatory autoimmune effect on human cells caused by nucleic acid ligands;
 b. inhibits bacteria-induced inflammatory effect; and
 c. demonstrates increased direct killing of Gram-negative bacteria compared to the native cathelicidin.

In some embodiments, the aforementioned pharmaceutical composition demonstrates increased direct killing of Enterobacteriaceae family bacteria.

In some embodiments, the pharmaceutical composition demonstrates increased direct killing of Gram-negative bacteria selected from the group consisting of *Klebsiella pneumonia, Serratia marcescens, Enterobacter cloacae, Escherichia coli* and *Pseudomonas aeruginosa*.

In some embodiments, the pharmaceutical composition comprising the modified peptide reduces red blood cell lysis and/or reduces cytotoxicity to cultured cells.

In some preferred embodiment, the aforementioned composition of bacteriocidal peptide has aromatic residues from said native cathelicidin replaced by polar or nonpolar residues.

In some preferred embodiment, the aforementioned composition of bacteriocidal peptide is selected from the group consisting of SMAP 29B/C/D (SEQ ID NOs: 24-26).

In some preferred embodiment, the aforementioned composition of bacteriocidal peptide has at least 95% identity to a peptide selected from the group consisting of SMAP 29B/C/D (SEQ ID NOs: 24-26).

This disclosure also provides a method of designing a bacteriocidal peptide from a native cathelicidin protein with the following properties:
    a. lacks pro-inflammatory effect with nucleic acid ligands;
    b. inhibits bacteria-induced inflammatory effect; and
    c. demonstrates increased direct killing of Gram-negative bacteria compared to the native cathelicidin;
In some embodiment, the aforementioned method comprising the steps of providing at least 30% of positively charged amino acid residues clustered within the N-terminal sequence of the peptide, and no more than 10% of negatively-charged amino acid residues in the entire peptide; replacing aromatic residues with polar or non-polar amino acids to reduce red blood cell lysis and/or cytotoxicity to cultured cells.

This disclosure also provides a method of identifying a native cathelicidin-derived peptide that is bacatericidal to treat bacterial infection. The method comprises:
    a. Providing a first concentration of the native cathelicidin-derived peptide to a subject that is infected by at least one Gram-negative bacteria;
    b. providing the subject a second concentration of antibiotics; and
    c. observing the additive or synergistic bacterial killing effect of steps a and b.

In some embodiment, the aforementioned method identifies a bacteriocidal peptide when the antibiotics concentration is zero or the subject is resistant to the antibiotics.

In some embodiment, the aforementioned method identifies a bacteriocidal peptide has at least 30% of total residues that are positively charged basic amino acid residues clustered within N-terminal and no more than 10% acidic residues of the total sequence.

In some embodiment, the aforementioned method reduces the dosage of either bacteriocidal peptide or the antibiotics to a level less than each of them is used individually to effectively kill the bacteria.

In some embodiment, the aforementioned method uses antibiotics selected from the group consisting of bacterial translation inhibitors, bacterial topoisomerase inhibitors, and bacterial cell wall synthesis inhibitors. For example, the antibiotics can be selected from the group consisting of kanamycin, levofloxacin, and meropenem.

This method further provides a method of reducing the risk of antibiotics resistance to at least one Gram-negative bacteria. The method comprises the steps of:
    providing a first concentration of bacteriocidal peptide from any of aforementioned paragraphs to an subject being infected by at least one Gram-negative bacteria; and
    providing a second concentration of an antibiotic to this subject; the second concentration of the antibiotics is less than a third concentration of the same antibiotics that is effective to kill the Gram-negative bacteria when it is used alone to treat this same Gram-negative bacteria.

The following numbered embodiments are contemplated and are non-limiting:
1. A pharmaceutical composition comprising:
    a modified peptide, wherein the modified peptide comprises
    an N-terminal sequence comprising basic residues,
    wherein the modified peptide comprises limited acidic residues.
2. The pharmaceutical composition of clause 1, wherein the N-terminal sequence is about 10% to about 50% of the total residues of the modified peptide.
3. The pharmaceutical composition of clause 1 or 2, wherein the N-terminal sequence is about 20% to about 50% of the total residues of the modified peptide.
4. The pharmaceutical composition of any one of clauses 1 to 3, wherein the N-terminal sequence is about 30% to about 50% of the total residues of the modified peptide.
5. The pharmaceutical composition of any one of clauses 1 to 4, wherein the N-terminal sequence is about 30% of the total residues of the modified peptide.
6. The pharmaceutical composition of any one of clauses 1 to 4, wherein the N-terminal sequence is about 50% of the total residues of the modified peptide.
7. The pharmaceutical composition of any one of clauses 1 to 6, wherein the N-terminal sequence comprises about 10% to about 65% positively charged basic residues.
8. The pharmaceutical composition of any one of clauses 1 to 6, wherein the N-terminal sequence comprises about 20% to about 65% positively charged basic residues.
9. The pharmaceutical composition of any one of clauses 1 to 6, wherein the N-terminal sequence comprises about 20% to about 50% positively charged basic residues.
10. The pharmaceutical composition of any one of clauses 1 to 6, wherein the N-terminal sequence comprises at least 30% positively charged basic residues.
11. The pharmaceutical composition of any one of clauses 1 to 10, wherein the acidic residues are less than 10% of the total residues.
12. The pharmaceutical composition of any one of clauses 1 to 11, wherein the basic residues are positively charged at physiological pH.
13. The pharmaceutical composition of any one of clauses 1 to 12, wherein the basic residues are selected from the group consisting of lysine, arginine, and histidine.
14. The pharmaceutical composition of any one of clauses 1 to 12, wherein the acidic residues are aspartic acid or glutamic acid.
15. The pharmaceutical composition of any one of clauses 1 to 14, wherein the modified peptide is derived from a native cathelicidin.
16. The pharmaceutical composition of clause 15, wherein the modified peptide has polar or non-polar residues in place of the aromatic residues of the native cathelicidin.
17. The pharmaceutical composition of clause 15, wherein the polar residues are selected from the group consisting of glutamine, asparagine, histidine, serine, threonine, cysteine, lysine, histidine, and arginine.
18. The pharmaceutical composition of clause 17, wherein the non-polar residues are selected from the group consisting of alanine, leucine, isoleucine, glycine, valine, methionine, and proline.
19. The pharmaceutical composition of any one of clauses 15 to 18, wherein the native cathelicidin is selected from the mammal group consisting of horse, pig, cow, sheep, goat, rhesus monkey, human, rabbit, mouse, rate and guinea pig.
20. The pharmaceutical composition according to any one of clauses 15 to 19, wherein the native cathelicidin is selected from the group consisting of eCATH-1 (SEQ ID NO: 13), eCATH-2 (SEQ ID NO: 10), eCATH-3 (SEQ ID NO: 9), PMAP-23 (SEQ ID NO: 11), PMAP-36 (SEQ ID NO: 14), PMAP-37 (SEQ ID NO: 8), BMAP-27 (SEQ ID NO: 16), BMAP-28 (SEQ ID NO: 12), BMAP-34 (SEQ ID NO: 7), SMAP-29 (SEQ ID NO: 15), SMAP-34 (SEQ ID NO: 6), chMAP-28, chMAP-34, RL-37 (SEQ ID NO: 2), LL-37 (SEQ ID NO: 1), hCAP-18, CRAMP (SEQ ID NO: 4), rCRAMP, CAP-11 (SEQ ID NO: 5) and CAP-18 (SEQ ID NO: 3).

21. The pharmaceutical composition of clause 1, wherein the modified peptide is selected from the group consisting of SEQ ID NO: 24, SEQ ID NO: 25, and SEQ ID NO: 26.

22. The pharmaceutical composition of clause 1, wherein the modified peptide has at least 95% identity to a peptide selected from the group consisting of SEQ ID NO: 24, SEQ ID NO: 25, and SEQ ID NO: 26.

23. The pharmaceutical composition of any one of clauses 1 to 22, wherein the modified peptide is a bacteriocidal peptide.

24. The pharmaceutical composition of any one of clauses 1 to 23, wherein the modified peptide lacks pro-inflammatory autoimmune effect on human cells caused by nucleic acid ligands.

25. The pharmaceutical composition of any one of clauses 1 to 24, wherein the modified peptide inhibits a bacteria-induced inflammatory effect.

26. The pharmaceutical composition of any one of clauses 1 to 25, wherein the modified peptide demonstrates increased direct killing of Gram-negative bacteria compared to the native cathelicidin.

27. The pharmaceutical composition of clause 26, wherein the Gram-negative bacteria is in the Enterobacteriaceae family.

28. The pharmaceutical composition of clause 27 or 28, wherein the Gram-negative bacteria is selected from the group consisting of *Klebsiella pneumonia, Serratia marcescens, Enterobacter cloacae, Escherichia coli,* and *Pseudomonas aeruginosa*.

29. The pharmaceutical composition of any one of clauses 1 to 28, wherein the modified peptide reduces red blood cell lysis and/or reduces cytotoxicity to cultured cells.

30. A method of designing a bacteriocidal peptide from a native cathelicidin protein, comprising
  providing a peptide comprising at least 30% of positively charged amino acid residues within an N-terminal sequence of the peptide, and less than 10% of negatively charged amino acid residues in the peptide;
  replacing aromatic residues in the peptide with polar or non-polar amino acids to reduce red blood cell lysis and/or cytotoxicity to cultured cells.

31 The method of clause 30, wherein the bacteriocidal peptide lacks a pro-inflammatory effect with nucleic acid ligands.

32. The method of clause 30 or 31, wherein the bacteriocidal peptide inhibits a bacteria-induced inflammatory effect.

33. The method of any one of clauses 30 to 33, wherein the bacteriocidal peptide demonstrates increased direct killing of Gram-negative bacteria compared to the native cathelicidin.

34. The method of any one of clauses 30 to 33, wherein the Gram-negative bacteria is in Enterobacteriaceae family.

35. The method of any one of clauses 30 to 34, wherein the Gram-negative bacteria is selected from the group consisting of *Klebsiella pneumonia, Serratia marcescens, Enterobacter cloacae, Escherichia coli,* and *Pseudomonas aeruginosa*

36. A method of designing a bacteriocidal peptide from a native cathelicidin peptide, comprising
  providing a native cathelicidin peptide having an N-terminal sequence;
  replacing residues in the N-terminal sequence with basic residues so that the N-terminal sequence comprises at least 25% basic residues.

37. The method of clause 36, further comprising replacing aromatic residues with polar or non-polar amino acids to reduce red blood cell lysis and/or cytotoxicity to cultured cells.

38. The method of clause 36 or 37, further comprising replacing acidic residues with residues selected from the group consisting of basic residues, neutral residues, aromatic residues, polar residues, and non-polar residues.

39. A method of identifying a bacteriocidal peptide to treat a bacterial infection in a subject, the method comprising:
  providing a first concentration of a bacteriocidal peptide to a subject that is infected by at least one Gram-negative bacteria;
  providing the subject a second concentration of antibiotic; and
  observing the additive or synergistic bacterial killing effect,
  wherein the bacteriocidal peptide is derived from a native cathelicidin peptide.

40. The method according to clause 39, wherein the subject is resistant to antibiotics.

41. The method of clause 39 or 40, wherein the bacteriocidal peptide comprises an N-terminal sequence comprising basic residues, and wherein the bacteriocidal peptide comprises limited acidic residues.

42. The method of clause 41, wherein the N-terminal sequence is about 10% to about 50% of the total residues of the modified peptide.

43. The method of clause 41 or 42, wherein the N-terminal sequence comprises about 10% to about 65% positively charged basic residues.

44. The method of clauses 41, 42, or 43, wherein the acidic residues are less than 10% of the total residues.

45. The method of any one of clauses 39 to 44, wherein the the first peptide concentration is less than a third concentration of the bacteriocidal peptide, wherein the third concentration is the concentration that is effective alone at killing the Gram-negative bacteria.

46. The method of any one of clauses 39 to 45, wherein the second concentration of the antibiotic is less than a fourth concentration of the antibiotic, wherein the fourth antibiotic is the concentration that is effective alone at killing the Gram-negative bacteria alone.

47. The method of any one of clauses 39 to 46, wherein the native cathelicidin peptide is selected from the group consisting of eCATH-1 (SEQ ID NO: 13), eCATH-2 (SEQ ID NO: 10), eCATH-3 (SEQ ID NO: 9), PMAP-23 (SEQ ID NO: 11), PMAP-36 (SEQ ID NO: 14), PMAP-37 (SEQ ID NO: 8), BMAP-27 (SEQ ID NO: 16), BMAP-28 (SEQ ID NO:
  12), BMAP-34 (SEQ ID NO: 7), SMAP-29 (SEQ ID NO: 15), SMAP-34 (SEQ ID NO: 6), chMAP-28, chMAP-34, LL-37 (SEQ ID NO: 1) RL-37 (SEQ ID NO: 2), hCAP-18, CRAMP (SEQ ID NO: 4), rCRAMP, CAP-11 (SEQ ID NO: 5) and CAP-18 (SEQ ID NO: 3).

48. The method of any one of clauses 39 to 48, wherein the bacteriocidal peptide is selected from the group consisting of SEQ ID NO: 24, SEQ ID NO: 25, and SEQ ID NO: 26.

49. A method of treating a subject infected with at least one Gram-negative bacteria using a bacteriocidal peptide, the method comprising:
  providing a first concentration of the bacteriocidal peptide to the subject, wherein the bacteriocidal peptide comprises an N-terminal sequence comprising basic residues, and wherein the bacteriocidal peptide comprises limited acidic residues.

50. The method of clause 49, further comprising providing the subject a second concentration of an antibiotic.

51. The method of clause 49 or 50, further comprising observing the additive and/or synergistic bacterial killing effect of the bacteriocidal peptide and the antibiotic.

52. The method of clause 48, 49, or 50, wherein the bacteriocidal peptide is selected from the group consisting of SEQ ID NO: 24, SEQ ID NO: 25, and SEQ ID NO: 26

53. The method of any one of clauses 49 to 52, wherein the subject is resistant to antibiotics.

54. The method of any one of clauses 49 to 53, wherein the first concentration is less than a third concentration of the bacteriocidal peptide, wherein the third concentration of bacteriocidal peptide is a concentration that is effective alone at killing the Gram-negative bacteria alone.

56. The method of clause 48 or 49, wherein the second concentration of antibiotic is less than a fourth concentration of antibiotic, wherein the fourth concentration of antibiotic is a concentration that is effective alone at killing the Gram-negative bacteria alone.

57. The method of any one of clauses 50, 51, and 56, wherein the antibiotic is selected from the group consisting of bacterial translation inhibitors, bacterial topoisomerase inhibitors, bacterial cell wall synthesis inhibitors, and mixtures thereof.

58. The method of any one of clauses 50, 51, 56, or 57, wherein the antibiotic is selected from the group consisting of kanamycin, levofloxacin, meropenem, and mixtures thereof.

59. A method of reducing the risk of antibiotics resistance, comprising
administering of a first concentration of a pharmaceutical composition of clause 1 to a subject being infected by at least one Gram-negative bacteria; and
administering a second concentration of an antibiotic to the subject;
wherein the second concentration of the antibiotic is less than a third concentration of the antibiotic, wherein the third concentration of antibiotic is a concentration that is effective alone at killing the Gram-negative bacteria alone.

60. A pharmaceutical formulation comprising the pharmaceutical composition of clause 1.

61. The pharmaceutical formulation of clause 60, further comprising a pharmaceutically acceptable carrier.

62. A lyophilisate or powder of the pharmaceutical formulation of clause 60.

These and other features, aspects, and advantages of the present invention will become better understood with reference to the following figures, associated descriptions and claims.

BRIEF DESCRIPTION OF FIGURES

FIG. 1. Shows cathelicidin peptides produced by different animals. FIG. 1A. A phylogenetic relationship of cathelicidin peptides from mammals. The figure is derived from results of Zanetti et al (J. Leuk. Biol. 2004). FIG. 1B. Names, lengths and sequences of cathelicidin peptides. The residues predicted to form an alpha-helix is underlined. The positively-charged residues are colored blue, the negatively-charged residues are colored red. Aromatic residues are in green.

FIG. 2. Shows cathelicidin peptides from animals have reduced ability to activate signal transduction in response to nucleic acids but can inhibit signaling in response to bacterial lipopolysaccharides.

FIG. 4. Shows negatively-charged residues in peptides can decrease antibacterial activity without increasing lysis of RBCs.

FIG. 5. Shows RBC lysis does not correlate with antibacterial activity. FIG. 5A. Peptides rank ordered for RBC lysis and their antibacterial activity. Residues in the peptides that are basic and aromatic are in blue and green, respectively.

FIG. 6. Shows highly effective antibacterial peptides can be modified to reduce cytotoxicity to mammalian cells. FIG. 6A. SMAP-29 (SEQ ID NO: 15) and its derivatives that have reduced RBC lysis retain antibacterial activity. SMAP-29B (SEQ ID NO: 24) and SMAP-29D (SEQ ID NO: 26) have substitutions of the one aromatic amino acid residue of SMAP-29 (SEQ ID NO: 15). The positively-charged amino acids are in blue, the aromatic amino acids are in green and the substitutions are in red. FIG. 6B. The ability of the SMAP29 series of peptides for enhancement of signal transduction by TLR3 and to suppress signal transduction by TLR4. IL-6 levels secreted by the cells were quantified using an ELISA assay.

FIG. 7. Shows peptides that are unable to enhance TLR3 and TLR9 signaling are also decreased for the association of the FRPL-1 receptor that promotes nucleic acid-peptide endocytosis.

FIG. 8. Shows Table 1.

Figure 2A:
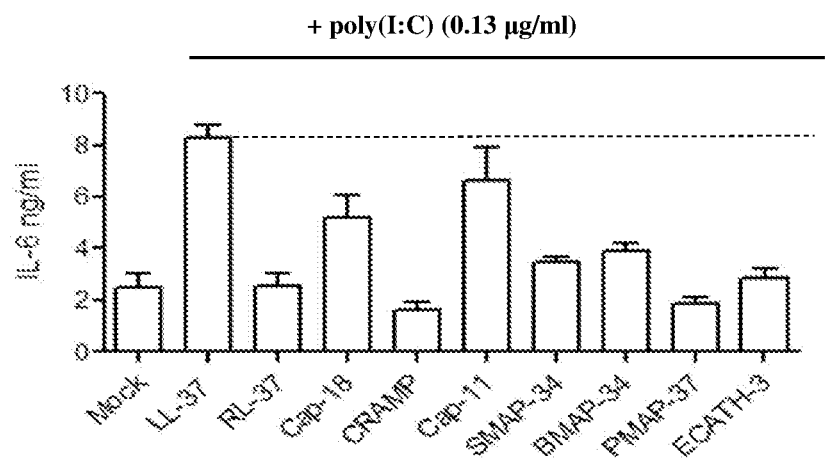
FIG. 2A. Innate immune signaling by endogenous Toll-like receptor 3 (TLR3) in BEAS-2B cells in response to double-stranded RNA and various bacteriocidal peptides. IL-6 cytokine produced in response to signal transduction by TLR3 and the double-stranded RNA mimic, poly(I:C), was quantified using ELISA. Where present, the peptides were added to the media of BEAS-2B cells to a final concentration of 2 µM. The dashed line demarcates the level of the proinflammatory IL-6 produced in the absence of LL-37 (SEQ ID NO: 1) enhancement of signal transduction. In the presence of LL-37 (SEQ ID NO: 1), IL-6 levels are enhanced by two-fold. All assays were performed in three independent samples and the mean and one standard error is shown above the bars.

BRIEF DESCRIPTION OF SEQUENCE LISTINGS, NAMES, AND SEQUENCES of PEPTIDES TESTED IN THIS WORK.

| | | |
|---|---|---|
| SEQ ID NO: 1 | LL-37 | LLGDFFRKSKEKIGKEFKRIVQRIKDFLRNLVPRTES |
| SEQ ID NO: 2 | RL-37 | RLGNFFRKVKEKIGGGLKKVGQKIKDFLGNLVPRTAS |
| SEQ ID NO: 3 | CAP-18 | GLRKRLRKFRNKIKEKLKKIGQKIQGLLPKLAPRTDY |
| SEQ ID NO: 4 | CRAMP | GLLRKGGEKIGEKLKKIGQKIKNFFQKLVPQPEQ |
| SEQ ID NO: 5 | CAP-11 | GLRKKFRKTRKRIQKLGRKIGKTGRKVWKAWREYGQIPYPCRI |
| SEQ ID NO: 6 | SMAP-34 | GLFGRLRDSLQRGGQKILEKAERIWCKIKDIFR |
| SEQ ID NO: 7 | BMAP-34 | GLFRRLRDSIRRGQQKILEKARRIGERIKDIFRG |
| SEQ ID NO: 8 | PMAP-37 | GLLSRLRDFLSDRGRRLGEKIERIGQKIKDLSEFFQS |
| SEQ ID NO: 9 | eCATH-3 | KRFHSVGSLIQRHQQMIRDKSEATRHGIRIITRPKLLLAS |
| SEQ ID NO: 10 | eCATH-2 | KRRHWFPLSFQEFLEQLRRFRDQLPFP |
| SEQ ID NO: 11 | PMAP-23 | RIIDLLWRVRRPQKPKFVTVWVR |
| SEQ ID NO: 12 | BMAP-28 | GGLRSLGRKILRAWKKYGPIIVPIIRIG |
| SEQ ID NO: 13 | eCATH-1 | KRFGRLAKSFLRMRILLPRRKILLAS |
| SEQ ID NO: 14 | PMAP-36 | VGRFRRLRKKTRKRLKKIGKVLKWIPPIVGSIPLGCG |
| SEQ ID NO: 15 | SMAP-29 | RGLRRLGRKIAHGVKKYGPTVLRIIRIAG |
| SEQ ID NO: 16 | BMAP-27 | GRFKRFRKKFKKLFKKLSPVIPLLHLG |
| SEQ ID NO: 17 | LL-29 | LLGDFFRKSKEKIGKEFKRIVQRIKDFLR |
| SEQ ID NO: 18 | CAP-11V1 | GLRKKFRKTRKRIQKLGRKIGKTGRKVWKAWREY |
| SEQ ID NO: 19 | LL-29V2 | LLGAFFRKSKEKIGKAFKRIVQRIKDFLR |
| SEQ ID NO: 20 | LL-29V | LLGAFFRKSKAKIGKAFKRIVQRIKAFLR |
| SEQ ID NO: 21 | SMAP-29V | RGLRRLGRKIAHEVKKYGPTVLRDIRIAG |
| SEQ ID NO: 22 | CAP11-V3 | GLRKKFRETRKEIQKLGEKIGKTGRKVWKDWREYGQIPYPCRI |
| SEQ ID NO: 23 | CAP11-V2 | GLRKKFRETRKEIQKLGKTGRKVWKAWREYGQIPYPCRI |
| SEQ ID NO: 24 | SMAP-29B | RGLRRLGRKIAHGVKKCGPTVLRIIRIAG |
| SEQ ID NO: 25 | SMAP-29C | RGLRRLGRKIAHGVKKCGPTVLRIIRIAGC |
| SEQ ID NO: 26 | SMAP-29D | RGLRRLGRKIAHGVKKLGPTVLRIIRIAG |

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person of ordinary skill in the art pertaining to this disclosure.

There is an urgent need to develop novel antimicrobials due to the rapid emergence of antibiotic-resistant bacteria. Antimicrobial peptides (AMPs) are produced by organisms in all three kingdoms of life on earth to decrease the establishment of other microbes. Cathelicidins are a class of peptides typically of ~25-40 amino acids in length that have a high frequency of basic amino acids. They interact with the membranes of susceptible bacteria, form higher order structures to cause leakage of ions and the death of the bacteria. Cathelicidins may also bind bacterial cell wall materials, including lipopolysaccharide (LPS) molecules that are potent inducers of the inflammatory responses. These properties have made AMPs attractive molecules to replace antibiotics.

LL-37 (SEQ ID NO: 1) is the only cathelicidin molecule produced by humans. The 37-residue LL-37 (SEQ ID NO: 1) is generated by proteolytic cleavage of the C-terminal portion of the hCAP-18 protein. As is the case with AMPs, LL-37 (SEQ ID NO: 1) has a large array of biological activities. For example, in addition to suppressing bacterial infection and suppressing the pro-inflammatory responses, LL-37 (SEQ ID NO: 1) can promote wound healing and decrease fibrosis.

The majority of the basic residues in LL-37 (SEQ ID NO: 1) had been determined to form an amphipathic alpha helix that may interact to form higher order structures. The C-terminal region of LL-37 (SEQ ID NO: 1) has a stretch of ~8 residues that are intrinsically disordered. LL-37 orthologs from other animals have a similar predicted structure, although the density of the positively-charged residues, the number of acidic residues and the length of the predicted disordered residues differed (FIG. 1A).

The LL-37 orthologs from several animals contain similar characteristics as LL-37 (SEQ ID NO: 1). Illustratively, many of them have a high abundance of basic amino acids (FIGS. 1A and 1B).

It is believed that the various activities of LL-37 (SEQ ID NO: 1) and the orthologs are at least partially associated with their concentration present in a given system. For example, in the presence of infection, circulating levels of LL-37 (SEQ ID NO: 1) in the blood can increase by over ten-fold. This increase has been correlated with diseases such as lupus and psoriasis, likely due to the activation of innate immune receptors that recognize nucleic acid ligands, such as TLR3 and TLR9. These pro-inflammatory properties of LL-37 (SEQ ID NO: 1) and cathelicidins, and the associated cytotoxicity to humans prevented LL-37 (SEQ ID NO: 1) or the likes will be detrimental for treating bacterial infections in humans.

Therefore, while antimicrobial peptides such as LL-37 (SEQ ID NO: 1) hold significant promise as bacteriocides for therapeutic uses, some activities that have prevented their use. One of these is that AMPs can have high levels of cytotoxicity and potentially negative pro-inflammatory effects. As described above for the cathelicidin LL-37 (SEQ ID NO: 1), elevated levels of LL37 have been linked to diseases such as systemic lupus, which likely results in the innate immune receptors such as Toll-like receptor 9. It is believed Toll-like receptor 9 recognizes DNA released from necrotic cells. LL-37 (SEQ ID NO: 1) can also activate the inflammatory response through TLR3 leading to detrimental effects to cells.

For more discussion of inflammatory responses caused by LL-37 or the like in immune response, and their related mechanism, see our patent application PCT/US2015/031928, filed on May 21, 2015. The content of which is incorporated herein entirely by reference. PCT/US2015/031928 seeks to balance the complex activity that cathelicidin proteins may have on human cells. For example, antagonists of LL-37 or the like can neutralize the detrimental effects of these cathelicidin proteins on the immune system. PCT/US2015/031928 falls short of completely abolish such negative effects of LL-37 or the likes.

How to remove the negative effects of antimicrobial peptides such as LL37 and the orthologs has not been previously determined.

Fortunately, not all cathelicidins appear to share the same suite of activities. CRAMP (SEQ ID NO: 4), the mouse ortholog of LL-37, was found to be unable to activate signaling by TLR3 in both mouse cells and in human cells. Previous studies demonstrated the mouse CRAMP (SEQ ID NO: 4) was unable to bind dsRNA and deliver the dsRNA to endosomes containing TLRs (Singh et al., 2013). However, CRAMP (SEQ ID NO: 4) retained the ability to suppress inflammatory response that is induced by lipopolysaccharide.

Accordingly, it may be possible that despite the fact that the cathelicidins have similar sequences and proposed structures (FIG. 1), some may have attributed more useful as antimicrobial peptides. This observation contemplates whether cathelicidins from other animals can be engineered to effectively kill bacteria and suppress the inflammatory responses associated with bacterial molecules, but not promote the inflammatory responses associated with nucleic acid ligands.

As described herein, features of potent bacteriocidal peptides derived from a native cathelicidin were identified. In some embodiments, the potent bacteriocidal peptides have reduced red blood cell lysis, reduced cytotoxicity to human cells, increased direct killing of Gram-negative bacterium with or without corresponding effective antibiotics, reduced cathelicidin dosage to achieve bacteria killing effect, reduced and low nucleic acid binding and can repress the inflammatory response caused by bacterial cell wall components.

Structural features of a strong bacteriocidal peptide derived from a native cathelicidin were identified. This includes but not limited to clustered positively-charged amino acids within the N-terminal of the sequence and low or no acidic amino acids in the entire sequence. In some embodiments, preferred amino acid substitutions from the native cathelicidin is provided. For example, SMAP-29D (SEQ ID NO: 26) and SMAP-29B (SEQ ID NO: 24), modified peptides from SMAP-29, have a tyrosine replaced with cysteine or leucine, which results in reduced red blood cell lysis. Preferred percentage of basic amino acid within the N-terminal sequence and acidic amino acid within the entire sequence of a strong antimicrobial peptide is provided as a guidance of designing such engineered peptides.

Briefly, it was discovered that multiple peptides from one organism can have very different activities. For example, horse eCATH-1, 2 and 3 have different bacterial killing ability (FIG. 3A). Given that the peptides have multiple functions, including antimicrobial activity, suppression of inflammatory response to bacterial ligands, possible roles in promoting inflammatory responses, this may suggest that some organisms may have multiple peptides that have specialized functions. It may be a misnomer to call all of these peptides antimicrobial peptides.

An examination of the peptides structure provided some general guidance for those cathelicidins having strong bacteriocidal activity. As will be exemplified below, the intrinsically disordered sequence is not important for antimicrobial activity. However, it was found that a clustering of basic residues within the N-terminal region of the peptide will increase bacteriocidal activity. In addition, the presence of acidic residues may decrease bacteriocidal activity.

Modified peptides comprising acidic residues in the N-terminal sequence may have bacteriocidal activity. As described herein, the N-terminal sequence is a portion of the amino acid sequence comprising the N-terminus of the peptide. The N-terminal sequence may be a percentage of the total residues of the peptide. In some embodiments, the N-terminal sequence may be one of the following values: about 10%, about 15%, about 20%, about 25%, about 30%, about 35%, about 40%, and about 50% of the total residues of the peptide. The N-terminal sequence percentage of the total residues may fall within one of many different ranges. In a set of ranges, the N-terminal sequence percentage is one of the following ranges:

about 10% to about 50%, about 15% to about 50%, about 15% to about 40%, about 20% to about 40%, and about 20% to about 35%.

In some embodiments, the N-terminal sequence of the modified peptide comprises acidic residues. In some embodiments, the acidic residues are selected from arginine (Arg, R), lysine (Lys, K), and histidine (His, H). In some embodiments, the acidic residues comprise functional groups capable of being positively charged at physiological pH. Representative acidic functional groups include amines, guanidines, and heteroaromatic rings capable of being ionized at physiological pH. It should be understood that acceptable peptide derivatives include D-amino acids, peptoids, synthetic peptides, and any suitable alternative thereof.

In some embodiments, the acidic residues of the N-terminal sequence comprise a percentage of the N-terminal sequence. In some embodiments, the acid residues are described as clustered within the N-terminal sequence. The percentage of acidic residues in the N-terminal sequence may be one of the following values: about 10%, about 15%, about 20%, about 25%, about 30%, about 35%, about 40%, about 50%, about 55%, about 60%, and about 65% of the total residues of the N-terminal sequence. In some embodiments, the acidic residues may be at least 10%, at least 15%, at least 20%, at least 30%, at least 35%, at least 40%, at least 45% and at least 45% of the total residues of the N-terminal sequence. The percentage of acidic residues of the N-terminal sequence may fall within one of many different ranges. In a set of ranges, the acidic residue percentage is one of the following ranges: about 10% to about 65%, about 10% to about 55%, about 15% to about 55%, about 20% to about 55%, about 20% to about 50%, about 25% to about 50%, about 25% to about 45%, about 25% to about 40%, and about 25% to about 35% of the total residues of the N-terminal sequence.

In some embodiments, basic residues are selected from aspartic acid (Asp, D) glutamic acid (Glu, E), and derivatives thereof. In some embodiments, basic residues comprise carboxylates or any other common functional group that is negatively charged at physiological pH. In some embodiments, the modified peptide comprises a percentage of basic residues. The percentage of basic residues of the total number of residues can be about 0, about 1%, about 2%, about 3%, about 4%, about 5%, about 6%, about 7%, about 8%, about 9%, about 10%, about 11%, about 12%, about 13%, about 14%, and about 15%, about 20%, and about 30%. In some embodiments, the percentage of the total residues that may be basic residues may be less than 30%, less than 25%, less than 20%, less than 15%, less than 10%, and less than 5%. In some embodiments, the modified peptide does not include a basic residue. The percentage of the basic residues of the modified peptides may fall within one of many different ranges. In a set of ranges, the basic residues are one of the following ranges:

about 0% to about 30%, about 0% to about 20%, about 2% to about 15%, about 2% to about 10%, and about 2% to about 5%.

In some embodiments, the modified peptide may be administered with an antibiotic. In some embodiments, the antibiotic is selected from the group consisting of bacterial translation inhibitors, bacterial topoisomerase inhibitors, bacterial cell wall synthesis inhibitors, and mixtures thereof. In some embodiments, the antibiotic is selected from the group consisting of kanamycin, levofloxacin, meropenem, and mixtures thereof.

Figure 5B:
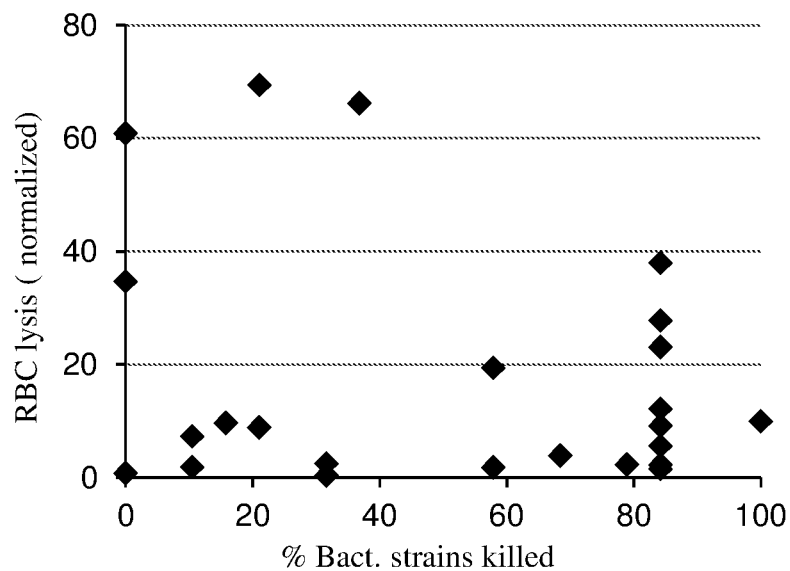
FIG. 5B. Graph of the relationship between antibacterial activity and RBC lysis. No obvious correlation exists.

Interestingly, the effective bacteriocidal activity does not correlate with higher mammalian cytotoxicity, as shown in FIG. 5B. This result indicates that highly effective bacteriocidal peptides can be further modified to minimize cytotoxicity to human cells without impairment of bacteriocidal activity.

Exemplified SMAP-29 derived peptides, sometimes called modified peptides, are shown in FIG. 6. These peptides show strong bacteriocidal activity against Gram-negative bacteria when used in concert with corresponding antibiotics or alone. An additive or synergistic effect in relation to antibiotics used alone was observed for these modified peptides. The synergistic indicators include reduced dosage of either the antimicrobial peptide, sometimes called a bacteriocidal peptide or a modified peptide, or antibiotics when used alone to treat bacterial infection. Such synergy leads to reduced red blood cell lysis and other detrimental inflammatory effects. Such detrimental inflammatory effects include but not limited to reduced IL-6 production in the presence of double-stranded RNA and enhanced suppression of the inflammatory response in the presence of LPS. Interestingly, these are fairly closely related phylogenetically. For these experiments, the main branch of the peptides that contained the human LL-37 (SEQ ID NO: 1) was found to have lower bacteriocidal activity.

The reduced dosage use for either the antimicrobial peptide or the antibiotic is significant in clinical perspective. For example, as discussed above, various cathelicidin activity properties are partly related to the concentrations of these proteins in a given system. Increased level of LL-37 (SEQ ID NO: 1) associated autoimmune disease effect could be decreased by the lack of the enhancement of the nucleic acid-induced inflammatory response and by the decreased effective concentration of the peptides for bacteriocidal activity.

Similarly, reducing antibiotic dosage in concert with the use of these modified peptides may minimize the risk of side effects of antibiotics.

Without being limited to the theory, the discovery of modified peptides that show the above-described properties may have a broad use in clinical therapeutics for bacterial infections, particularly those Gram-negative bacteria exemplified below. With the increasing risk of antibiotics resistance, an alternative solution to battle bacterial infection is in need. The present disclosure provides such opportunity to reduce the dosage use of antibiotics, and may also achieve even better result than the use of antibiotics.

The effects of the bacteriocidal activity relate to various species of bacterium, as will be exemplified below. Further examination these peptides' effects to each bacterial species may provide insights to alternative solutions to different diseases, which is of great medical value to the healthcare community.

The previously described embodiments of the pharmaceutical compositions are applicable to the method described herein. In various embodiments, the administration according to the described methods is an injection. In some embodiments, the injection is selected from the group consisting of intraarticular, intravenous, intramuscular, intradermal, intraperitoneal, and subcutaneous injections. In one embodiment, the injection is an intravenous injection.

In other various embodiments, the administration according to the described methods is performed as a single dose administration. In other embodiments, the administration according to the described methods is performed as a multiple dose administration.

In yet other embodiments, pharmaceutical formulations are provided. In one illustrative embodiment, the pharmaceutical formulation comprises any of the pharmaceutical compositions described herein. The previously described embodiments of the pharmaceutical compositions are applicable to the pharmaceutical formulations described herein.

The type of formulation employed for the administration of the compounds may be dictated by the particular compounds employed, the type of pharmacokinetic profile desired from the route of administration and the compound(s), and the state of the patient. The polypeptides may be formulated as pharmaceutical compositions for systemic administration. Such pharmaceutical compositions and processes for making the same are known in the art for both humans and non-human mammals. See, e.g., Remington: The Science and Practice of Pharmacy, (A. Gennaro, et al., eds., 19$^{th}$ ed., Mack Publishing Co., 1995).

In some embodiments, the pharmaceutical formulations described herein further comprise a pharmaceutically acceptable carrier. In some embodiments, the pharmaceutical formulations described herein further comprise a pharmaceutically acceptable diluent. Diluent or carrier ingredients used in the pharmaceutical compositions containing polypeptides can be selected so that they do not diminish the desired effects of the polypeptide. Examples of suitable dosage forms include aqueous solutions of the polypeptides, for example, a solution in isotonic saline, 5% glucose or other well-known pharmaceutically acceptable liquid carriers such as alcohols, glycols, esters, and amides.

As used herein, "carrier" refers to any ingredient other than the active component(s) in a formulation. Pharmaceutically acceptable carriers are determined in part by the particular composition being administered, as well as by the particular method used to administer the composition (see, e.g., Remington's Pharmaceutical Sciences, 17th ed. (1985)). The choice of carrier will to a large extent depend on factors such as the particular mode of administration, the effect of the carrier on solubility and stability, and the nature of the dosage form. In one illustrative aspect, the carrier is a liquid carrier.

As used herein, the term "pharmaceutically acceptable" includes "veterinarily acceptable", and thus includes both human and animal applications independently. For example, a "patient" as referred to herein can be a human patient or a veterinary patient, such as a domesticated animal (e.g., a pet).

In some embodiments, the pharmaceutical formulations described herein optionally include one or more other therapeutic ingredients. As used herein, the term "active ingredient" or "therapeutic ingredient" refers to a therapeutically active compound, as well as any prodrugs thereof and pharmaceutically acceptable salts, hydrates, and solvates of the compound and the prodrugs. Other active ingredients may be combined with the described polypeptides and may be either administered separately or in the same pharmaceutical formulation. The amount of other active ingredients to be given may be readily determined by one skilled in the art based upon therapy with described polypeptides.

In some embodiments, the pharmaceutical formulations described herein are a single unit dose. As used herein, the term "unit dose" is a discrete amount of the composition comprising a predetermined amount of the described polypeptides. The amount of the described polypeptides is generally equal to the dosage of the described polypeptides which would be administered to an animal or a convenient fraction of such a dosage such as, for example, one-half or one-third of such a dosage.

In one illustrative aspect, parenteral formulations may be suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art.

The aqueous preparations according to the invention can be used to produce lyophilisates by conventional lyophilization or powders. The preparations according to the invention are obtained again by dissolving the lyophilisates in water or other aqueous solutions. The term "lyophilization," also known as freeze-drying, is a commonly employed technique for presenting proteins which serves to remove water from the protein preparation of interest. Lyophilization is a process by which the material to be dried is first frozen and then the ice or frozen solvent is removed by sublimation in a vacuum environment. An excipient may be included in pre-lyophilized formulations to enhance stability during the freeze-drying process and/or to improve the stability of the lyophilized product upon storage. For example, see Pikal, M. *Biopharm.* 3(9)26-30 (1990) and Arakawa et al., *Pharm. Res.,* 8(3):285-291 (1991).

In one embodiment, the solubility of the polypeptides used in the preparation of a parenteral formulation may be increased by the use of appropriate formulation techniques, such as the incorporation of solubility-enhancing agents.

In various embodiments, formulations for parenteral administration may be formulated to be for immediate and/or modified release. Modified release formulations include delayed, sustained, pulsed, controlled, targeted and programmed release formulations. Thus, a polypeptide may be formulated as a solid, semi-solid, or thixotropic liquid for administration as an implanted depot providing modified release of the active compound.

The formulations can be presented in unit-dose or multi-dose sealed containers, such as ampules and vials. The formulations can also be presented in syringes, such as prefilled syringes.

In various embodiments, the dosages of the polypeptides can vary significantly depending on the patient condition and the severity of the disease to be treated. The effective amount to be administered to a patient is based on body surface area, patient weight or mass, and physician assessment of patient condition.

Suitable dosages of the polypeptides can be determined by standard methods, for example by establishing dose-response curves in laboratory animal models or in humans in clinical trials. Illustratively, suitable dosages of polypeptides (administered in a single bolus or over time) include from about 1 pg/kg to about 10 µg/kg, from about 1 pg/kg to about 1 µg/kg, from about 100 pg/kg to about 500 ng/kg, from about 1 pg/kg to about 1 ng/kg, from about 1 pg/kg to about 500 pg/kg, from about 100 pg/kg to about 500 ng/kg, from about 100 pg/kg to about 100 ng/kg, from about 1 ng/kg to about 10 mg/kg, from about 1 ng/kg to 1 mg/kg, from about 1 ng/kg to about 1 µg/kg, from about 1 ng/kg to about 500 ng/kg, from about 100 ng/kg to about 500 µg/kg, from about 100 ng/kg to about 100 µg/kg, from about 1 µg/kg to about 500 µg/kg, or from about 1 µg/kg to about 100 µg/kg. In each of these embodiments, dose/kg refers to the dose per kilogram of a patient's or animal's mass or body weight.

Materials and Methods

Cells and Reagents—

The BEAS-2B cell line was from the American Type Culture Collection and cultured in BEGM media with its supplements (11; Lonza). Peptides without or with covalently attached fluorophores were custom synthesized (Karybaybio) and purified to at least 95% purity. SiRNAs specific to FPRL1 (sc-40123), EGFR (sc-29301), or a nonspecific control siRNA (sc-37007) were from Santa Cruz Biotechnology.

Quantification of IL-6—

IL-6 production was quantified by ELISA using the OptEIA™ kit (BD Biosciences). A typical assay used $2 \times 10^4$ BEAS-2B cells/well grown for 24 h in flat bottom 96-well plates. Poly(I:C) was added to a final concentration of 0.13 µg/ml.

Data Analysis—

Peptide secondary structure was analyzed using the Jpred4 program (ref.). The intrinsically disordered residues were predicted using the program PONDR. All data shown are the means and ranges for one standard error for a minimal of three independent samples. Data sets were compared using the Student t-test calculated with GraphPad Prism 5 software.

MIC Determination—

Antimicrobial activity was determined using the broth microdilution method based on the general recommendation of the CLSI (ref. 1, 2, and 3). Bacteria were grown in Mueller-Hinton broth at 37° C. until $OD_{625}$ reaches to 0.06, and then bacteria were further diluted into 1:20 for later use. Peptides were diluted in Mueller-Hinton broth at concentrations of 1, 2, 4, 8, 16, and 32 µg/ml. 10 microliter (µL) of diluted bacteria was mixed with 90 µL of peptides at varying concentrations followed by incubation at 37° C. for 16-18 hours. The MIC is the lowest peptide concentration at which visible growth was inhibited. The MIC value was determined at least twice in independent experiments and typically in 3-4 assays.

Hemolytic Activity—

The hemolytic activities of peptides were determined using human red blood cells (hRBCs) (Innovative Research, Inc., cata # IPLA-WB3-18103). The hRBCs were washed three times with PBS and then resuspended in PBS. hRBCs solution was mixed with serial dilutions of peptides in PBS buffer. The reaction mixtures were incubated for 45 mins at 37° C. After centrifugation at 94×g for 10 min, the intact RBCs were pelleted and the hemoglobin released from RBCs was monitored by measuring the absorbance of the supernatant at 415 nm. The background level of absorbance was measured in sampled incubated with only PBS buffer. 100% hemolysis was determined in sampled incubated with water. The percentage of hemolysis was calculated according to the following equation.

$$\text{Percentage of hemolysis} = [(A_{sample} - A_{blank})/A_{water}] * 100\%$$

EXAMPLES

The following examples present features, aspects and advantages of the present invention. They are for illustrative purposes only. Any and all changes and modifications that come within the spirit of the disclosure are desired to be protected.

Example 1. Common Structure of Cathelicidin Peptides from Different Mammals

In this example, a phylogenetic relationship of cathelicidin peptides from various mammals is presented, as shown in FIG. 1A (derived from results of Zanetti et al (J. Leuk. Biol. 2004). SEQ ID NOs: 1-16 representing cathelicidin peptides that are found in human, Rhesus monkey, Rabbit, mouse, Guinea pig, sheep, cow, pig and horse, respectively. It is known in general that there are positively charged residues, and negatively charged residues in cathelicidin peptides. Aromatic peptides also present in these peptides, sometimes more than one of them.

The activity properties of these peptides are being investigated, and a correlation of their structural basis may illustrate the structural requirements to produce a strong bacteriocidal peptide, as illustrated below in further examples.

SEQ ID Nos: 17-26 represent cathelicidin peptides that have been engineered. In some embodiments, these peptides may be referred to as modified peptides, engineered peptides, or bacteriocidal peptides. These modified peptides amino acids changes, deletions or other changes that are man-made relative to the native cathelicidin. In some embodiments, the bacteriocidal activity of these peptides and the cytotoxicity to human cells may be different than those of the corresponding native cathelicidin peptide.

Figure 2B:
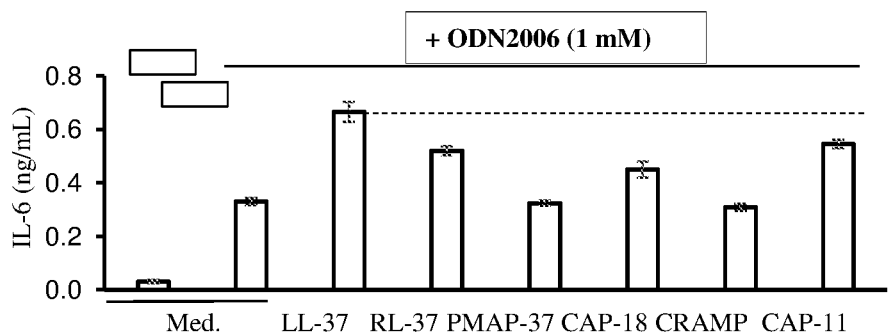
FIG. 2B. Innate immune signaling by endogenous TLR9 in BEAS-2B cells in response to CpG DNA ODN2006 in the absence and presence of peptides. The format of the experiment is identical to those in panel A.

Example 2. The Antimicrobial Peptides have Reduced Nucleic Acid Associated Pro-Inflammation Effect on Cultured Cells The activity of SEQ ID Nos 1-9's activity from Example 1 was investigated. Some peptides demonstrate a reduced ability to activate signal transduction in response to nucleic acids in cultured cells BEAS-2B (which expresses endogenous TLR3 and TLR9), as shown in FIGS. 2A and 2B. This effect is illustrated by the IL-6 production level in response to the addition of either poly I:C double-strand RNA mimic that activates TLR3, or ODN2006 single-strand DNA agonist for TLR9. For peptides showing reduced IL-6 production in response to the nucleic acids, they have a reduced pro-inflammatory effect, presumably through interference of signal transduction pathway of endogenous TLR3 or TLR9 in the cultured cell line.

Figure 7A:
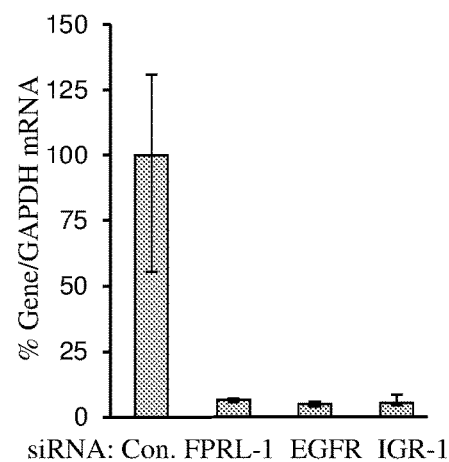
FIG. 7A. Quantification of the reduction in the mRNA levels of three known receptors that interact with LL-37 (SEQ ID NO: 1) after siRNA knockdown. BEAS-2B cells were transfected with siRNA at 0.3 nM for 48 h, followed by extraction of the mRNAs and RT-PCR to quantify the individual RNAs. GAPDH from each sample was also quantified to allow normalization of the RNAs.
Figure 7B:
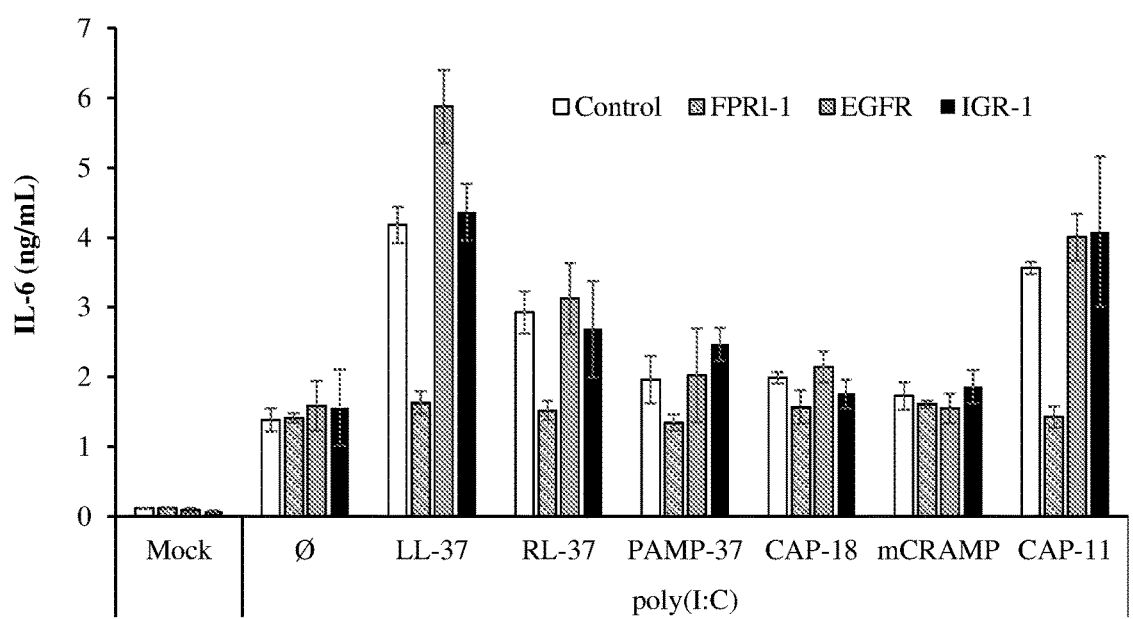
FIG. 7B. The peptides that retain partial enhancement of TLR3 signaling (RL-37 (SEQ ID NO: 2) and CAP-11 (SEQ ID NO: 5)) require the FPRL-1 receptor. The mock samples were not treated with the dsRNA mimic, poly(I:C) or peptide.

Without being limited to the theory, the TLR3 and TLR9 pathways are associated with the expression of the FPRL-1 receptor, as shown in FIGS. 7A and 7B Several of the LL-37 orthologs were examined for the ability to modulate pro-inflammatory IL-6 cytokine production in the presence of nucleic acid ligands in BEAS-2B cells, a lung epithelial BEAS-2B cell line. BEAS-2B cells express multiple TLRs and using this cell line, LL-37 (SEQ ID NO: 1) has been shown to bind to the nucleic acids, direct them to endocytose and then enhance the signal transduction by TLR3 (Singh et al., 2013, 2014). The activity of the TLR can be assessed by the secretion the pro-inflammatory cytokines, including interleukin 6 (IL-6). In the presence of the double-stranded RNA (dsRNA) mimic, poly(I:C), 2 µM of LL-37 (SEQ ID NO: 1) increased IL-6 product by two-fold of the level of poly(I:C) alone in ELISA assays. Consistent with previous results, CRAMP (SEQ ID NO: 4) was unable to enhance IL-6 production over a range of concentrations (FIG. 2A). Interestingly, the cathelicidins from Guinea pig, CAP-11 (SEQ ID NO: 5) retained reduced levels of activation of TLR3 in comparison to LL-37 (SEQ ID NO: 1) while the peptides from pig (PMAP-37 (SEQ ID NO: 8)), horse (eCATH-3 (SEQ ID NO: 9)) and cow (BMAP-34 (SEQ ID NO: 7)) were more similar to CRAMP (SEQ ID NO: 4). Similar responses were observed with BEAS-2B cells treated with the TLR9 agonist and the various peptides (FIG. 2B). These results show that among the peptides tested, cathelicidins from other species have reduced levels of activation of the TLR3 and TLR9 when compared to LL-37 (SEQ ID NO: 1).

Example 3. The Antimicrobial Peptides can Suppress LPS Induced Inflammation

In this example, the activity of peptides of SEQ ID Nos 1-9's from Example 1 were investigated and found the majority have the ability to suppress signal transduction in response to bacterial lipopolysaccharide (LPS) in cultured cells BEAS-2B (which expresses endogenous TLR4). LPS, also called endotoxin, is an important determinant in an immune system over-reaction to bacterial infection. The over-reaction can lead to inflammation and shock.

Figure 2C:
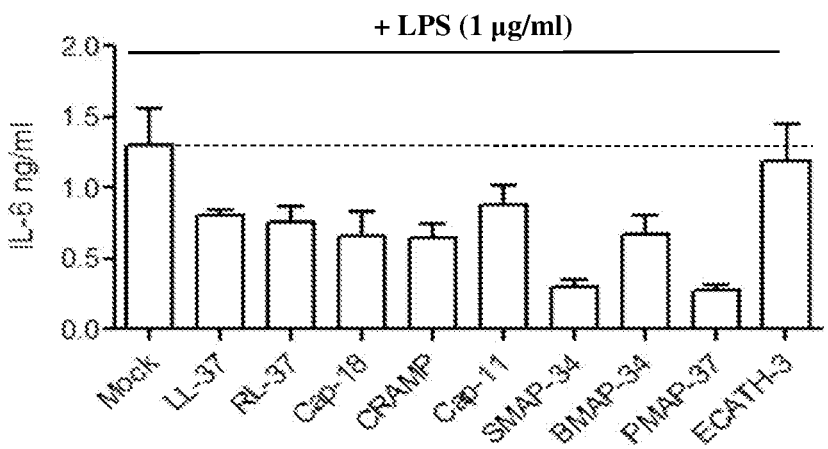
FIG. 2C The cathelicidin peptides from different mammals all retain the ability to suppress the production of the IL-6 cytokine induced by TLR4 in the presence of the LPS. The format of the experiment is identical to those in FIG. 2A.

An important activity of LL-37 (SEQ ID NO: 1) is that it can bind to LPS and suppress the inflammatory response induced by the TLR4. The peptides from different animals were examined to determine if the peptides share this activity by analyzing IL-6 production induced by LPS. The addition of 2 µM of LL-37 (SEQ ID NO: 1) to the cells inhibited IL-6 production (FIG. 2C). The cathelicidin orthologs from other animals also inhibited IL-6 production in response to LPS and to more dramatic levels. The ability to suppress the LPS-induced inflammatory response is thus a more highly conserved activity of the cathelicidins. Furthermore, it should be possible to identify cathelicidin peptides with the combinations of properties suitable for the development of antimicrobials.

Thus, those peptides that were tested for their ability to inhibit signaling in response to bacterial lipopolysaccharides (LPS) in cultured BEAS-2B cells (which have TLR4 expression, leading to LPS induced inflammation). This effect was also measured by IL-6 production level in the presence of LPS and the peptide being investigated. See FIG. 2C. It is worth noting that all peptide in 2A and 2B that have reduced IL-6 expression level, also showed reduced IL-6 level caused by LPS. This indicates that these peptides maintained their inhibitory effect to LPS induced inflammation in these cultured cells, presumably through the inhibition of TLR-4 pathway.

Thus it is possible to identify peptides that are less pro-inflammation among cathelicidin peptides.

Example 4. Bacteriocidal Activities of the Cathelicidin Peptides

LL-37 (SEQ ID NO: 1) can lyse bacteria and to suppress sepsis in animal models. However, LL-37 (SEQ ID NO: 1) concentrations in excess to 10 µM were typically used in those experiments and higher concentrations of LL-37 (SEQ ID NO: 1) are also associated with inflammation-associated responses, such as psoriasis. The antimicrobial activities of LL-37 (SEQ ID NO: 1) were tested against 19 selected strains of Gram-negative bacteria. The bacteria included 2 *Enterobacter cloacae*, 6 strains of *Escherichia coli*, 4 *Klebsiella pneumonia*, 4 *Pseudomonas aeruginosa* and 3 *Serratia marcescens*. At least 32 µg/ml of LL-37 (SEQ ID NO: 1), corresponding to ~8 µM, is needed to inhibit the growth of any of the 19 bacterial strains (Table 1 (FIG. 8)). These results show that LL-37 (SEQ ID NO: 1) is unlikely to be useful as an antimicrobial peptide.

Despite LL-37 (SEQ ID NO: 1) being not promising as the bacteriocidal peptide, many other cathelicidin peptides and related peptides produced by animals had useful antibacterial activity. See FIG. 3A. The tested bacterium species tested were: *Klebsiella pneumonia, Serratia marcescens, Enterobacter cloacae, Escherichia coli* and *Pseudomonas aeruginosa*. When tested at 16 μg/ml, which corresponds to ~4 μM the peptides had an inhibitory activity that ranged from 0 to 17 of the Gram-negative bacteria. Notably, the inhibitory activity is not correlated with the source of the peptides. Of the three peptides from horse, eCATH-3 (SEQ ID NO: 9) did not inhibit the growth of any of the 19 strains while eCATH-1 (SEQ ID NO: 13) inhibited 11 strains (FIG. 3A). When the bacterial cultures were plated in the absence of peptides, no growth was observed, demonstrating that the peptides were bacteriocidal. Similarly, the bovine BMAP-28 (SEQ ID NO: 12) inhibited 9 strains while BMAP-27 (SEQ ID NO: 16) inhibited 17 strains. Notably, the porcine PMAP-36 (SEQ ID NO: 14), the guinea pig CAP-11 (SEQ ID NO: 5) and sheep SMAP-29 (SEQ ID NO: 15), and the bovine BMAP-27 (SEQ ID NO: 16) had the most potent antibacterial activities. Some of the peptides had minimal inhibitory concentrations of 4 or 8 mg/ml for several bacterial species.

Further investigation to dissect the differences that may cause this disparity among different cathelicidin peptide is illustrated in the following examples.

Example 4. AMP Properties Correlated with Antibacterial Activity

In this example, features of the peptides that can be correlated with bacteriocidal activity were identified. The majority of the peptides had a disordered sequence near the C-terminal region of the peptide. In LL-37 (SEQ ID NO: 1), this sequence was associated with binding to nucleic acid and is required for the trafficking of the peptide-dsRNA complex into endosomes. The presence of the predicted disordered sequence in the AMPs did not appear to correlate with antimicrobial activity (FIG. 3A). For example, LL-37 (SEQ ID NO: 1) that has an 8-residue disordered tail did not inhibit any of the 19 strains while CAP-11 (SEQ ID NO: 5), which has a 9-residue disordered tail, inhibited 16 of the 19 strains.

To determine whether the disordered region affected antimicrobial activity, LL-29 (SEQ ID NO: 17), which lacked the disordered 8-residues at the C-terminal region of LL-37 (SEQ ID NO: 1) was tested. Secondary structure prediction showed that LL-29 (SEQ ID NO: 17) retains the majority of the α-helical region of LL-37 (SEQ ID NO: 1). LL-29 (SEQ ID NO: 17) was modestly increased for antibacterial activity when compared to LL-37 (SEQ ID NO: 1), inhibiting 3 of the 19 strains (FIG. 3A). A variant of the CAP-11 peptide that lacked the C-terminal 9 disordered sequence, CAP-11V1 (SEQ ID NO: 18), was tested and found that it inhibited 16 of the 19 strains, the same as CAP-11 (SEQ ID NO: 5). However, for several of the strains, CAP-11V1 (SEQ ID NO: 18) did reduce the minimal inhibitory concentration (MIC) for the bacteria (Table 1 (FIG. 8). With both LL-37 (SEQ ID NO: 1) and CAP-11 (SEQ ID NO: 5), the presence of the disordered sequence does not appear to be required to inhibit bacteria and may even prevent optimal inhibition.

Figures 3B, 3C:
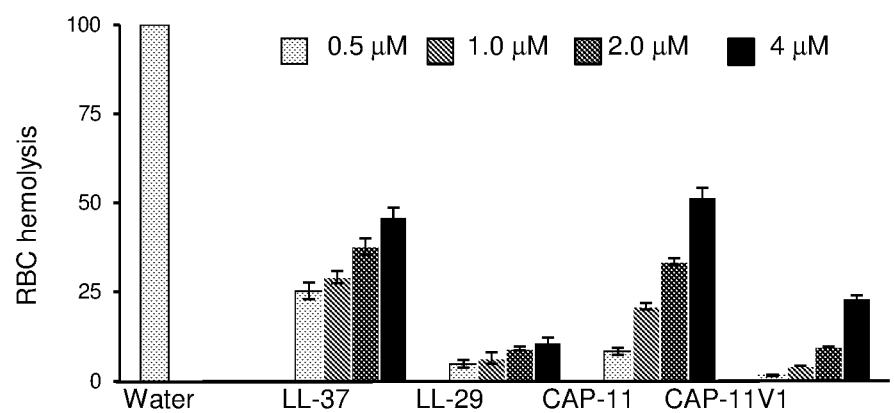
FIG. 3B. Sequences predicted to be intrinsically disordered does not contribute to the bacteriocidal activity. LL-37 (SEQ ID NO: 1) and CAP-11 (SEQ ID NO: 5) that have C-terminal disordered residues. LL-29 (SEQ ID NO: 17) and CAP-11V1 (SEQ ID NO: 18) have the disordered sequence removed. Numbers of 19 strains of bacteria from five species inhibited at 16 µg/ml are listed.
FIG. 3C. Removal of the C-terminal intrinsically disordered residues in LL-37 (SEQ ID NO: 1) and CAP-11 (SEQ ID NO: 5) did not result in increased lysis of human RBCs. The concentrations of the peptides tested and the effect on hemoglobin release are shown. The background level for hemolysis was typically at 1-2% of the level observed when the RBCs were incubated in water. The results shown have the background levels subtracted. All samples were tested in triplicates and the bars show the mean level of hemolysis and the range for one standard deviation of the data.

Whether the disordered sequence in LL-37 (SEQ ID NO: 1) and CAP-11 (SEQ ID NO: 5) affected the lysis of red blood cells (RBCs) was examined. The addition of LL-37 (SEQ ID NO: 1) resulted in RBC lysis in a concentration-dependent manner (FIG. 3C). Interestingly, LL-29 (SEQ ID NO: 17) that lacked the disordered tail was reduced in RBC lysis. Similarly, the removal of the disordered sequence of CAP-11 (SEQ ID NO: 5) resulted in decreased RBC lysis (FIG. 3C). These results show that the disordered sequences in LL-37 (SEQ ID NO: 1) and CAP-11 (SEQ ID NO: 5) can contribute to RBC lysis.

Figure 3D:
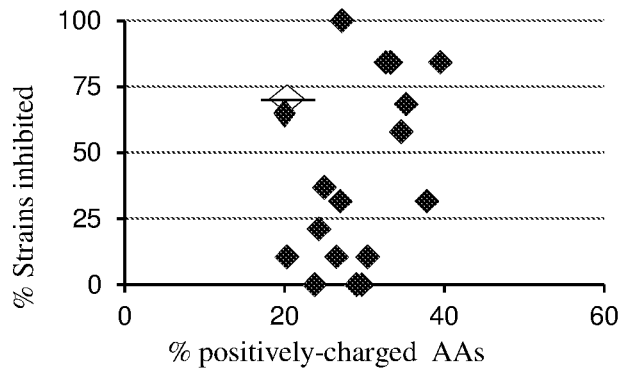
FIG. 3D. The percent of positively-charged amino acids in the peptides does not correlate with the antibacterial activity of the peptides. E) The density of the positively-charged amino acids in the peptides correlates with the antibacterial activity. The lower line contains the average of the positively-charged amino acids starting from the N-terminal residue from the four least effective antibacterial peptides, LL-37 (SEQ ID NO: 1), eCATH-3 (SEQ ID NO: 9), SMAP-34 (SEQ ID NO: 6) and eCATH-2 (SEQ ID NO: 10). The upper line contains the average positive-charge residues of the four most effective antibacterial peptides, PMAP-36 (SEQ ID NO: 14), CAP-11 (SEQ ID NO: 5), SMAP-29 (SEQ ID NO: 15) and BMAP-27 (SEQ ID NO: 16). In each graph, each data point represents the sum total charge of four residues starting at the N-terminal residue (position 1) of a peptide. Arginines and lysines are counted as a +1 while histidines are counted as 0.5.
Figure 3E:
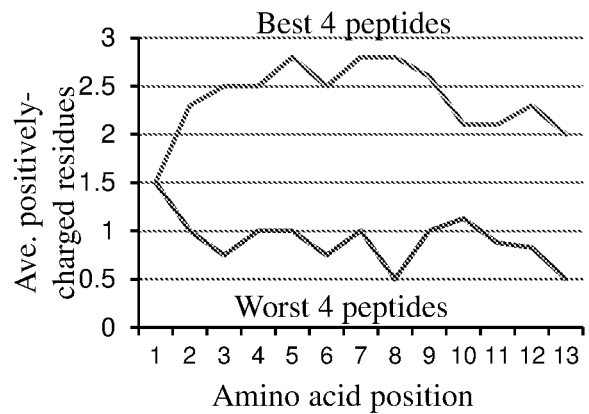
FIG. 3. Antibacterial activity of a panel of peptides produced by mammals.
FIG. 3A. Peptides and the antibacterial activities against 19 different Gram-negative bacteria. The positively-charged and negatively-charged residues in the peptides are colored, blue and red, respectively. The underlined residues are predicted to form α-helical structures. The bacteria species tested are: *Klebsiella pneumonia* (*K. p.*), *Serratia marcescens* (*S. m.*), *Enterobacter cloacae* (*E. cl.*), *Escherichia coli* (*E. co.*) and *Pseudomonas aeruginosa* (*P. a.*). Inhibition of bacteria growth was determined by the microdilution assay with the peptides being present at 16 µg/ml, which corresponds to approximately 2× the minimal inhibitory concentration (MIC) for the majority of the peptides. The MICs for several of the peptides are shown in Table 1 (FIG. 8).
FIG. 3F. A correlation between the presence of negatively-charged amino acids being detrimental for antimicrobial activity. Percentages are calculated as the frequency of aspartates and glutamates relative to the total length of the peptide.
Figure 3F:
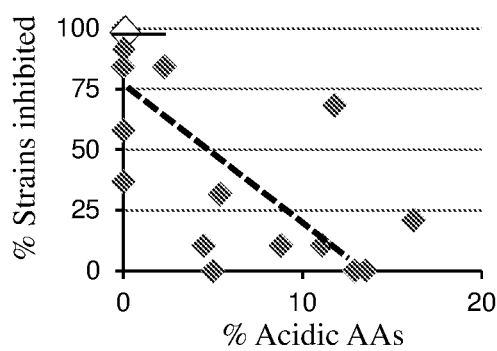

The amino acid compositions of the peptides were examined for correlation with antibacterial activity. All of the peptides had a fairly high percentage of basic residues and the overall number of positively-charged amino acids in the peptides did not show a strong correlation with antibacterial activity (FIG. 3D). However, the peptides that were ineffective for antibacterial activity had positively-charged amino acids that are evenly distributed along the peptide length while the more effective antibacterial peptides had more dense clusters of basic amino acids near the N-terminal sequence of the peptides (FIG. 3E). In addition, the more potent antimicrobial peptides (AMPs) also had relatively few acidic residues. In fact, PAMP-36, SMAP-29 (SEQ ID NO: 15) and BMAP-27 (SEQ ID NO: 16) that all inhibited 16 or more of the 19 bacterial strains lacked any acidic residues while CAP-11 (SEQ ID NO: 5), which inhibited 16 of the strains, had only one acidic residue and it is near the C-terminal portion of the peptide (FIG. 3A). Further, a general correlation exists in that the peptides with a higher proportion of acidic residues had a lower number of bacterial strains inhibited (FIG. 3F).

Figures 4A, 4B:
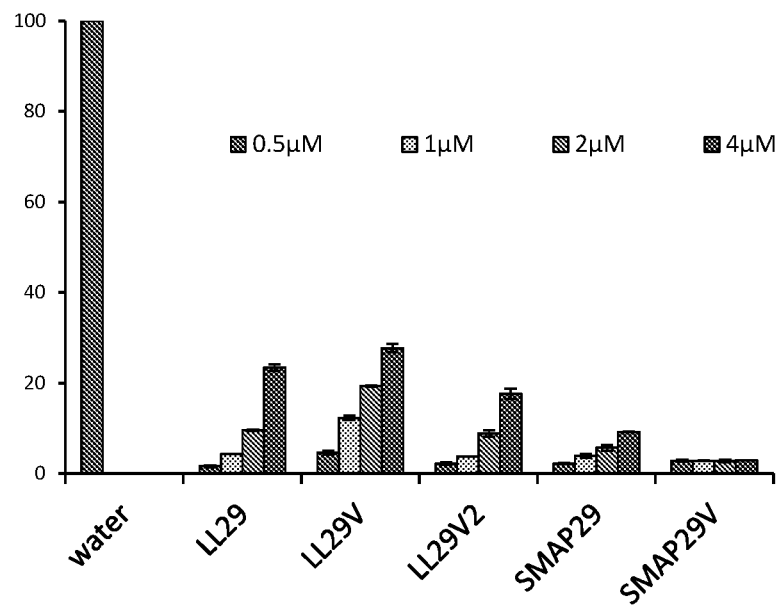
FIG. 4A. Replacement of negatively-charged residues in LL-29 (SEQ ID NO: 17) with neutral amino acids can increase antibacterial activity. The acidic residues are in red and the replacements are in bold, black letters. The bacterial strains tested are the standard 19 used in all of these studies: *Klebsiella pneumonia* (*K. p.*), *Serratia marcescens* (*S. m.*), *Enterobacter cloacae* (*E. cl.*), *Escherichia coli* (*E. co.*) and *Pseudomonas aeruginosa* (*P. a.*).
FIG. 4B. Effects of the § abundance of negatively charged residues in peptides on RBC lysis. Each bar represents three independent samples.

To examine further whether the antimicrobial activity will be affected by the presence of negatively-charged amino acids, the abundance of negatively-charged residues were altered in several peptides and tested them for antibacterial activity (FIG. 4). A variant of LL-29 that replaced two of the four negatively-charged amino acids, LL-29V2 (SEQ ID NO: 19) was found to inhibit one additional strain of bacteria when compared to LL-29 (SEQ ID NO: 17). More dramatically, replacing all four negatively-charged residues in LL-29 inhibited 11 strains of bacteria instead of the four by LL-29 (SEQ ID NO: 17) (FIG. 4A). Interestingly, *Klebsiella pneumoniae* was the species most affected by the negatively-charged residues. LL-29V (SEQ ID NO: 20) was able to inhibit all four of the *K. pneumonia* strains tested (FIG. 4A; Table 1 (FIG. 8)).

SMAP-29 (SEQ ID NO: 15), one of the most effective antibacterial peptides, had no acidic residues. To examine the effects of negatively-charged residues in AMP on bacteriocidal activity further, a variant of SMAP-29 named SMAP-29V (SEQ ID NO: 21) that has two negatively-charged residues (FIG. 4A) was tested. While SMAP-29 (SEQ ID NO: 15) was able to inhibit 16 of 19 strains, SMAP-29V (SEQ ID NO: 21) was able to inhibit 13 strains (FIG. 4A, Table 1 (FIG. 8)). Along with the results from variants of LL-29, these results confirm that the presence of negatively-charged residues in the peptides could decrease bacteriocidal activity.

Whether the LL-29 and SMAP-29 variants altered the lysis of RBCs was examined. LL-29V2 (SEQ ID NO: 19) (with 2 negatively-charged residues had a slightly increased RBC lysis while LL-29V (SEQ ID NO: 20) (without negatively-charged residues) had comparable levels of RBC lysis as LL-29 (SEQ ID NO: 17) (FIG. 4B). SMAP-29 that lacked any negatively-charged residues had fairly low levels of RBC lysis compared to LL-37 (SEQ ID NO: 1) and the addition of two negatively-charged residues did not affect RBC lysis. These results suggest that the presence of negatively-charged residues that decrease antibacterial activity, does not correlate to RBC lysis.

Thus from this example, it is apparent that a cathelicidin peptide having a good bacteriocidal activity requires a cluster of positively-charged basic residues within the N-terminal seqeunce of the peptide, no or low acidic amino acids in the entire sequence. Additionally, the red blood cell lysis is not correlated to acidic amino acids in the sequence.

A rough percentage of positively charged basic amino acid within the N-terminal of an antimicrobial sequence is determined by at least 30% of positively charged within N-terminal and no more than 10% of acidic amino acid throughout the entire sequence of the antimicrobial peptide.

Example 6. Properties AMPs and RBC Lysis

In this example, it was confirmed that there is no correlation between the degree of RBC lysis and bacteriocidal activity. Additionally, it was revealed for the first time that peptide with higher or lower aromatic residues may have lower RBC lysis.

RBC lysis for several peptides at 2 µM concentration (FIG. 5A) was measured. There was no relationship between antibacterial activity and RBC lysis. In fact, several of the peptides that were the least effective in antibacterial activity actually had higher levels of RBC lysis (FIG. 5B). The results suggest that the design of effective bacteriocidal peptides could avoid negatively-charged residues.

Figure 5C:
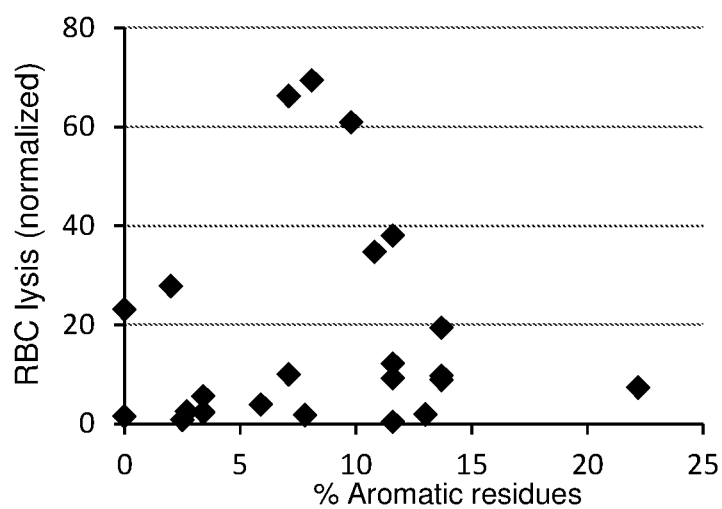
FIG. 5C. Peptides with a higher degree of RBC lysis have an intermediate level of aromatic residues.

Whether correlation(s) exist between RBC lysis and the sequence of the residues was investigated. The peptides with lower RBC lysis tended to have positively-charged residues clustered near their N-terminal regions (FIG. 5A). Also, peptides that had lower RBC lysis tended to have either higher or lower levels of aromatic residues (FIG. 5C). Thus to avoid RBC lysis, one strategy might be replacing aromatic residues with non-polar or polar amino acids, as exemplified below for SMAP-29 B and D.

Example 7. Engineered AMPs with Reduced Toxicity for Mammalian Cells

In this example, engineered antimicrobial peptide derived from the native cathelicidin peptides were made and tested their functionality including associated RBC lysis, direct bacterial killing, and other features according to the observation in the above examples.

The lack of a correlation between effective bacterial killing and RBC lysis suggests that changes in the peptides could be made to reduce RBC lysis without compromising bacteriocidal activity. The SMAP-29 (SEQ ID NO: 15) peptide ready had lower RBC lysis when compared to LL-37 (SEQ ID NO: 1) (FIG. 6A). Two variants were made that replaced the tyrosine residue within SMAP-29 with wither a cysteine (SMAP-29B (SEQ ID NO: 24)) or a leucine (SMAP-29D (SEQ ID NO: 26)) and tested the peptides for antimicrobial activity and RBC lysis. Both SMAP-29B (SEQ ID NO: 24) and SMAP-29D (SEQ ID NO: 26) were reduced for RBC lysis without a significant loss in bacteriocidal activity.

In addition, peptides SMAP-29B (SEQ ID NO: 24) and SMAP-29D (SEQ ID NO: 26) also demonstrated reduced cytotoxicity to red blood cells compared to SMAP-29 (SEQ ID NO: 15) that did not have the tyrosine replacement by non-polar or polar amino acids (FIG. 6A).

Example 8. Confirmation of Lower Activation of TLRs with IL-6 Assays in Engineered Antimicrobial Peptides In this example, the engineered peptides from Example 7 were tested for their reduced activation of TLRs, the latter may lead to pro-inflammation responses in cultured cells. The IL-6 expression was measured as discussed in the material method section. FIG. 6B illustrates that the effective bacterial killing antimicrobial peptides such as SMAP29-B and SMAP29-D have reduced TLR3 signal transduction in the presence of double-stranded RNA that is associated with pro-inflammation responses. At the same time, SMAP-29B (SEQ ID NO: 24) and SMAP-29D (SEQ ID NO: 26) retained their ability to suppress TLR4 signal transduction that is associated with LPS-induced IL-6 production that is also linked to the suppression of the inflammatory response.

Example 9. Effects of the Peptides on Gram-Positive Bacteria

In this example, antimicrobial peptide effects were measured on a number of Gram-negative bacteria (Table 1 (FIG. 8)) and a number of Gram-positive bacteria (Table 2). The effect is shown by the lowest peptide concentration at which visible Gram-negative or Gram-positive bacterium growth was inhibited. The peptides tested in Table 1 uniformly indicates that Gram-negative bacterium responded well to the engineered peptides in Example 6 (being inhibited at lower concentrations of these tested peptides), whereas Gram-positive bacteria responded poorly to all the engineered peptides from Example 6, if at all (not being inhibited at all or requires much higher concentration of peptides). Thus it is fairly certain that antimicrobial peptides similarly engineered as those from Example 6, will be less likely to work on killing Gram-positive bacteria.

TABLE 2

MIC of select peptides to four strains of Gram-positive bacteria.

| | MIC (µg/ml) | | | |
|---|---|---|---|---|
| Peptide | E. faecalis 51299 | E. fecalis 29212 | S. aureus 25923 | S. aureus 29213 |
| BMAP27 | >32 | >32 | 16 | 16 |
| CAP-11 | >32 | >32 | 32 | 32 |
| CAP-11V1 | >32 | >32 | 32 | 32 |
| CAP-11V2 | >32 | >32 | >32 | >32 |
| CAP-11V3 | >32 | >32 | >32 | >32 |
| SMAP-29 | 32(8) | 32(16) | 8 | 8 |
| SMAP-29B | >32 | >32 | >32 | >32 |
| SMAP-29C | 32 | 32 | 8 | 8 |

TABLE 2-continued

MIC of select peptides to four strains of Gram-positive bacteria.

| | MIC (µg/ml) | | | |
|---|---|---|---|---|
| Peptide | E. faecalis 51299 | E. fecalis 29212 | S. aureus 25923 | S. aureus 29213 |
| SMAP-29D | 32 | >32 | 16 | 16 |
| SMAP-29V | >32 | >32 | >32 | >32 |

Example 10. Effects on Gram-Negative Bacteria in Connection with Use of Antibiotics In this example, the combined use of a bacteriocidal peptide with an antibiotics to treat certain species of Gram-negative bacterium was evaluated (Table 1 (FIG. 8)). The minimum required concentration of either the bacteriocidal peptide (in this case SMAP-29C (SEQ ID NO: 25)) or the antibiotics (in these cases kanamycin, Levofloxacin (LVX), and Meropenem (MEM)) has become equal to or less than ½ MIC when they were used separately to treat the named bacterium (Tables 3, 4, 5). That is, SMAP-29 C concentration is equal to or less than ½ MIC when combined with antibiotics, and Kan, LVX, and MEM concentration is equal to ½ MIC when combined with SMAP-29C (SEQ ID NO: 25) peptide.

TABLE 3

The MIC for MAP-29C when combined with Kanamycin.

| | | | | | SMAP-29C | | | |
|---|---|---|---|---|---|---|---|---|
| Organism | IU or OC# | Kan* (µg/ml) | MIC for SMAP-29C alone (µg/ml) | MIC for ShpC + Kan* (ug/ml) | MIC fold change | Kan (µg/ml) | Kan + SMAP-29C* (µg/ml) | Kan MIC Fold change |
| E. cloacae | OC 4080 | 1 | 4 | 2 | ↓2x | 2 | <0.25 | ↓>8x |
| E. coli | ATCC25922 | 1 | 4 | <0.25 | ↓16x | 2 | <0.25 | ↓>8x |
| E. coli | IU-342 | 8 | 4 | 2 | ↓2x | 16 | 8 | ↓2x |
| K. pneumoniae | OC 4110 | 2 | 8 | 2 | ↓4x | 4 | 2 | ↓2x |
| P. aeruginosa | PA01 oprD | 32 | 8 | 2 | ↓4x | 64 | 32 | ↓2x |
| S. marcescens | 4104 | 2 | >16 | 2 | ↓>8x | 4 | 2 | ↓2x |

TABLE 4

The MIC for MAP-29C when combined with Levofloxacin

| Organism | IU or OC# | LVX* (µg/ml) | MIC for SMAP-29C alone (µg/ml) | MIC for SMAP-29C + LVX* (µg/ml) | SMAP-29C MIC fold change | LVX (µg/ml) | LVX + SMAP-29C* (µg/ml) | LVX MIC fold change |
|---|---|---|---|---|---|---|---|---|
| E. cloacae | OC 4080 | 0.008 | 4 | 4 | 1x | 0.032 | <0.004 | ↓>8x |
| E. coli | ATCC 25922 | 0.016 | 4 | 4 | 1x | 0.016 | 0.016 | 1 |
| E. coli | IU-342 | 2 | 4 | 4 | 1x | 8 | 2 | ↓4x |
| K. pneumoniae | OC 4110 | 0.25 | 8 | 8 | 1x | 0.5 | 0.5 | 1 |
| P. aeruginosa | PA01 oprD | 2 | 8 | 8 | 1x | 4 | <0.125 | ↓>32x |
| S. marcescens | 4104 | 2 | >16 | 4 | ↓>4x | 4 | <0.125 | ↓>32x |

TABLE 5

The MIC for MAP-29C when combined with meropenem

| Organism | IU or OC# | MEM* (µg/ml) | MIC for SMAP-29C alone (µg/ml) | MIC for SMAP-29C + MEM (µg/ml) | SMAP-29C MIC fold change | MEM (µg/ml) | MEM + SMAP-29C* (µg/ml) | MEM MIC fold change |
|---|---|---|---|---|---|---|---|---|
| E. cloacae | OC 4080 | i | 4 | 2 | ↓>2x | 0.032 | 0.008 | ↓4x |
| E. coli | ATCC 25922 | 1 | 4 | | | 0.016 | 0.008 | ↓2x |
| E. coli | IU-342 | 8 | 4 | 4 | 1x | 0.016 | <0.004 | ↓>4x |
| K. pneumoniae | OC 4110 | 2 | 8 | 4 | ↓2x | 0.052 | 0.032 | 1x |
| P. aeruginosa | PA01 oprD | 32 | 8 | 4 | ↓2x | 1 | 0.5 | ↓2x |
| S. marcescens | 4104 | 2 | >16 | >16 | No change | 0.032 | 0.008 | ↓4x |

*SMAP-29C concentration is equal to or less than ½ MIC when combined with antibiotics
*Kan, LVX* and MEM* concentration is equal to ½ MIC when combined with SMAP-29C peptide.

This provides solid support that the exemplified bacteriocidal peptides or the likes can be used together with antibiotics to reduce both the dosage of bacteriocidal peptides and the dosage of antibiotics. Without being limited to the theory, the advantage of either dose reduction has significant value. For example, lower bacteriocidal peptide concentration in the treatment prevented TLR signaling pathway induced pro-inflammatory responses; lower the dose of antibiotics may delay or prevent the resistance development to these antibiotics. The fact that these antimicrobial peptides can even work in the absence of antibiotics, provides an opportunity for treating those bacterium that have already developed the resistance to certain antibiotics.

These and other features, aspects, and advantages of the present invention will become better understood with reference to the following figures, associated descriptions and claims.

All of the patents, patent applications, patent application publications and other publications recited herein are hereby incorporated by reference as if set forth in their entirety.

While the invention has been illustrated and described in detail in the foregoing description, such an illustration and description is to be considered as exemplary and not restrictive in character, it being understood that only the illustrative embodiments have been shown and described and that all changes and modifications that come within the spirit of the invention are described and included as further embodiments.

What is claimed:

1. A pharmaceutical composition comprising: a modified peptide selected from the group consisting of SEQ ID NO: 24, SEQ ID NO: 25, and SEQ ID NO: 26.

2. A method of treating a subject infected with at least one Gram-negative bacteria, the method comprising: administering a first concentration of the bacteriocidal peptide selected from the group consisting of SEQ ID NO: 24, SEQ ID NO: 25, and SEQ ID NO: 26.

3. The method of claim 2, wherein the subject is resistant to at least one antibiotic.

4. A method of reducing the risk of antibiotic resistance comprising administering the pharmaceutical composition of claim 1 to a subject infected by at least one Gram-negative bacteria; and administering an antibiotic to the subject.

* * * * *